US006849607B2

(12) United States Patent  (10) Patent No.: US 6,849,607 B2
Pandey et al.  (45) Date of Patent: Feb. 1, 2005

(54) GALECTIN RECOGNIZED PHOTOSENSITIZERS FOR PHOTODYNAMIC THERAPY

(75) Inventors: Ravindra K. Pandey, Williamsville, NY (US); Thomas J. Dougherty, Grand Island, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 10/141,241

(22) Filed: May 7, 2002

(65) Prior Publication Data

US 2002/0198157 A1 Dec. 26, 2002

Related U.S. Application Data

(60) Provisional application No. 60/289,750, filed on May 9, 2001.

(51) Int. Cl.[7] .................... A01N 43/04; C07H 15/00; A61B 5/055

(52) U.S. Cl. .................... 514/25; 514/32; 424/9.362; 424/9.61; 536/17.2; 536/17.3; 536/17.4; 540/145

(58) Field of Search .................... 514/25; 536/17.4; 540/145; 424/9.362

(56) References Cited

U.S. PATENT DOCUMENTS 5,952,366 A * 9/1999 Pandey et al.

FOREIGN PATENT DOCUMENTS

FR 2 709 491 3/1995
WO WO 99 67249 12/1999

OTHER PUBLICATIONS

Hombrecher et al., "Synthesis and Investigation of Galactopyranosyl–cholesteryloxy Substituted Porphyrin", Bioorganic and Medicinal Chemistry Letters, vol. 6, No. 11, 1996, pp. 1199–1202.*
Allen, Howard J., et al., "Role of Galaptin in Ovarian Carcinoma Adhesion to Extracellular Matrix in Vitro", Journal of Cellular Biochemistry, Jan. 17, 1990, pp 43–57, vol. 43.
Andre, S. et al., "Galectins–1 and –3 and their Ligands in Tumor Biology", J. Cancer Res. Clin. Oncol., 1999, pp 461–474, vol. 125. (Abstract only).
Bachor, R., et al., "Photosensitized Destruction of Human Bladder Carcinoma Cells Treated with Chlorine6–Conjugated Microspheres", Proc. Natl. Acad. Sci., 1991, pp 1580–1584, vol. 88. (Abstract only).
Barondes, S.H., et al., "Galectins: A Family of Animal β–Galactoside–Binding Lectins", Cell, 1994, pp 597–598, vol. 76.

Castronovo, V., "Laminin Receptors and Laminin–Binding Proteins During Tumor Invasion and Metastasis", Invasions & Metastasis, 1993, pp 1–30, vol. 13. (Abstract only).
Chen, Y., et al., "Use of Sialylated or Sulfated Derivatives and Acrylamide Copolymers of Gal Beta 1,3GalNAc Alpha–and GalNAc Alpha– to Determine the Specificieits of Anti–T and Anti–Tn Antibody Levels in Cancer Patients", Glycoconjugate Journal, 1995, pp 55–62, vol. 12.
Chiariotti, L., et al., "Increased Expression of the Negative Growth Factor, Galactoside–Binding Protein, Gene in Transformed Thyroid Cells, and in Human Thyroid Carcinoma", Oncogene, 1992, pp 2507–2511, vol. 7.
Chiariotti, L., et al., "Control of Galectin Gene Expression", Biochimie, 1999, pp 381–388, vol. 81.
Donald, P.J., et al., "Monoclonal Antibody–Porphyrin Conjugate for Head and Neck Cancer; The Possible Magic Bullet", Otolaryng Head Neck Surg., 1991, pp 781–787, vol. 105 (Abstract only).
Dougherty, T., et al., "Photodynamic Therapy", J. Natl. Cancer Inst. 1998, pp 889–905, vol. 90.
Engvall, E., "Enzyme Immunoassay ELISA and EMIT", Methods in Enzymology, 1980, pp 419–439, vol. 70.
Fingar V.H., et al., "Expression of Chemokine Receptors by Endothelial Cells: Detection by Intravital Microscopy Using Chemokine–Located Fluorescent Microspheres", Methods in Enzymology, 1997, pp 148–158, vol. 288.

(List continued on next page.)

Primary Examiner—James O. Wilson
Assistant Examiner—Traviss C. McIntosh, III
(74) Attorney, Agent, or Firm—Michael L. Dunn

(57) ABSTRACT

Purpurin-carbohydrate conjugates and their method of preparation and use for treatment of cancer cells. The conjugates have the general formula:

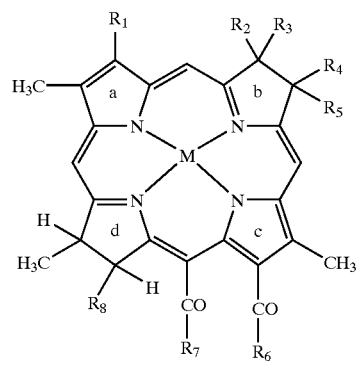

wherein $R_6$ and $R_7$ taken together are $=NR_{11}$ or are independently $—OR_{11}$, where at least one $R_{11}$ is preferably a mono or polysaccharide moiety and $R_1$–$R_8$ are various groups formed from carbon and hydrogen and optionally oxygen and nitrogen where $R_3$ and $R_4$ may together from a covalent bond.

25 Claims, 17 Drawing Sheets

OTHER PUBLICATIONS

Hemming, A.W., et al., "Photodynamic Therapy of Squamous Cell Carcinoma. An evaluation of a New Photosensitizing Agent, Benzoporphyrin Derivative and New Photoimmunoconjugate", Surg. Oncol., 1993, pp 187–196, vol. 2. (Abstract only).

Henderson, B., et al., "An in Vivo Quantitative Structure–Activity Relationship for a Congeneric Series of Pyropheophorbide Derivatives as Photosensitizers for Photodynamic Therapy", Cancer Research, 1997, pp 4000–4007, vol. 57.

Hombrecher, H., et al., "Synthesis and Investigations of a Galactopyranosyl–Cholesteryloxy Substituted Porphyrin" Bioorganic & Medicinal Chem. Letters, 1996, pp1199–1202, vol. 6, No. 11.

Illinger, D., et al., "The Kinetic Aspects of Intracellular Fluorescence Labeling with TMA–DPH Support the Maturation Model for Endocytosis in L929 Cells", The Journal of Cell Biology, 1994, pp 783–794, vol. 125 (Abstract only).

Karagianis, G., et al. "Biophysical and Biological Evaluation of Porphyrin–bisacridine Conjugates" Anti–Cancer Drug Design, 1996, pp 205–220, vol. 11 (Abstract only).

Kessel, D., et al., "Sites of Photodamage in vivo and in vitro by a Cationic Porphyrin", Photochem. Photobiol., 1995, pp 875–881, vol. 62 (Abstract only).

Kessel, D., et al., "Photodynamic Therapy: A Mitochondrial Inducer of Apoptosis" Cell Differ., 1999, pp 28–35, vol. 6 (Abstract only).

Kozyrev, A.N., et al., "Synthesis and Spectroscopic Studies of Novel Chlorins with Fused Quinoxaline or Benzimidazole Ring Systems and the Related Dimers with Extended Conjugation" Tetrahedron, 2000, pp 3353–3364, vol. 56.

Lahm, H., et al., "Comprehensive Galectin Fingerprinting in a Panel of 61 Human Tumor Cell Lines by RT–PCR and its Implications for Diagnostic and Therapeutic Procedures", J. Cancer. Res. Clin. Onco., 2001, pp 375–386, vol. 127 (Abstract only).

Leonidas, D.D., et al., "Structural Basis for the Recognition of Carbohydrates by Human Galectin–7", BIochemistry, 1998, pp 13930–13940, vol. 37.

Liotta, L.A., et al., "Tumor Invasion and Metastasis–Role of the Extracellular Matrix: Rhoads Memorial Award Lecture", Cancer Res., 1986, pp 1–7, vol. 46.

MacDonald, I., et al., "Subcellular Localization Patterns and their Relationship to Photodynamic Activity of Pyropheophorbide–a Derivatives", Photochemistry and Photobiology, 1999, pp 789–797, vol. 70.

Magnusson, G., et al., "BF3–Etherate Induced Formation of 2,2,2–Trichlorethyl–Glycopyranosides. Selective Visualization of Carbohydrate Derivatives on TLC Plates", Acta Chemica Scandinavica B, 1981, pp 213–221, vol. 35.

Morgan, J. et al., "Comparison of Photodynamic Targets in a Carcinoma Cell Line and its Mitochondrial DNA–Deficient Derivative", Photochem. Photobiol, 2000, pp 747–757, vol. 71.

Pandey, R.K., et al., "Alkyl Ether Analogs of Chlorophyll A Derivatives: Part 1, Synthesis, Photophysical Properties and Photodynamic Efficacy", Photochemistry and Photobiology, 1996, pp 194–204, vol. 64.

Prendergast, F.G., et al., "1–[4–(trimethylamino)–phenyl]–6–phenylhexa–1, 3, 5–triene: Synthesis, Fluorescence Properties and use as a Fluorescence Probe of :ipid Bilayers", Biochemistry, 1981, pp 7333–7338, vol. 20.

Rini, J.M., "Lectin Structures", Annu. Rev. Biophys. Biomol. Struct., 1995, pp 551–577, vol. 24.

Rungta, A., et al., "Purpurinimides as Photosensitizers: Effect of the Presence and Position of the Substituents in the In Vivo Photodynamic Efficacy", Biorg. Med. Chem. Lett., 2000, pp. 1463–1466, vol. 10.

Sacchettini, J.C., et al., "Multivalent Protein–Carbohydrate Interactions. A New Paradiagm for Supermolecular Assembly and Signal Transduction", Biochemistry, 2001, pp 3009–3015, vol. 40.

Salvatore, P., et al., "Galectin–1 Gene Expression and Methylation State in Human T Leukemia Cell Lines", International Journal of Oncology, 2000, pp 1015–1018, vol. 17.

Schmidt–Erfurth, U., et al., "Photodynamic Targeting of Human Retinoblastoma Cell Using Covalent Low Density Lipoprotein Conjugates", Br. J. Cancer, 1997, pp 54–61, vol. 75. (Abstract only).

Sears, P., et al., "Carbohydrate Mimetics: A New Strategy for Tackling the Problem of Carbohydrate–Mediated Biological Recognition", Angew. Chem. Intl. Ed. Eng., 1999, pp 2301–2324, vol. 38.

Smith, K.M., "Porphyrins and Metalloporphyrins", Elsevier Scientific Publications, Amsterdam, 1975, ISBN 044415378 (Table of Contents only).

Sol., V., et al., "Synthesis, Spectroscopy, and Photodytotoxicity of Glycosylated Amino Acid Porphyrin Derivatives as Promising Molecules for Cancer Phototherapy", J. Org. Chem., 1999, pp 4431–4444, vol. 64.

Van Den Brule, F.A., et al., "Expression of the 67 kD Laminin Receptor, Galectin–1, and galectin–3 in Advanced Human Uterine Adenocarcinoma", Human Pathology, 1996, pp 1185–1191, vol. 27. (Abstract only).

Vrouenraets, M.B., et al., "Development of Meta–Tetrahydroxyphenylchlorin–Monoclonal Antibody Conjugate for Photoimmunotherapy", Cancer Res., 1999, pp 1505–1513, vol. 59. (Abstract only).

Zheng, G., et al., "Novel Chlorin–Diene Bulding Block by Enyne Metathesis: Synthesis of Chlorin–Fullerene Dyads", Chem. Commun., 1999, pp 2469–2470.

Zheng, G., et al., "Photsensitizers Related to Purpurin–18–N–alkylimides: A Comparative in vivo Tumoricidal Ability of Ester Versus Amide Functionalities", Bioorg. Med. Chem. Lett., 2000, pp 123–127, vol. 10.

Zheng, G., et al., "Synthesis of β–Galactose–Conjugates Chlorins Derived by Enyne Methathesis as Galectin–Specific Photosensitizers for Photodynamic Therapy", J. Org. Chem., 2001, pp 8709–8716, vol. 66.

* cited by examiner

GALECTIN RECOGNIZED PHOTOSENSITIZERS FOR PHOTODYNAMIC THERAPY

This application claims priority from U.S. Provisional Patent Application No. 60/289,750 filed May 9, 2001.

BACKGROUND OF THE INVENTION

Photodynamic therapy (PDT), now a well recognized treatment for the destruction of tumors, utilizes the ability of a selectively retained photosensitizer to elicit an efficient photodynamic reaction upon activation with tissue penetrating light Pandey, R., Zheng, G. Porphyrins as Photosensitizers in Photodynamic Therapy, in *The Prophyrin Handbook* (Eds: Smith, K. M., Kadish, K., Guilard, R.) Academic Press, San Diego, 2000 Vol. 6; Sherman, W. M., Allen, C. M., van Lier, J. E., Role of Activated Oxygen Species in Photodynamic Therapy, Methods in Enzymology, 319, 376–400, 2000). Though a large number of porphyrin based photosensitizers have been reported since the introduction of the first PDT drug Photofrin®, there has not been much success on improving the photosensitizer's tumor selectivity and specificity because tumor cells in general have nonspecific affinity to porphyrins (Dougherty, T. J., Gomer, C., Henderson, B. W., Jori, G., Kessel, D., Kprbelik, M., Moan, J., Peng, Q., Photodynamic Therapy, J. Natl. Cancer Inst. 90, 889–905, 1998; Schmidt-Erfurth, U., Diddens, H., Birngruber, R., Hasan, T., Photodynamic Targeting of Human Retinoblastoma Cells Using Covalent Low Density Lipoprotein Conjugates, Br. J. Cancer, 75, 54–61, 1997; Finber, V. H., Guo, H. H., Lu, Z. H., Peiper, S. C., Expression of Chemokine Receptors by Endothelial Cells: Detection by Intravital Microscopy Using Chemokine-Located Fluorescent Microspheres, Methods in Enzymology, 288, 148–158, 1997). Although the mechanism of porphyrin retention by tumors is not well understood, the balance between lipophilicity and hydrophilicity is recognized as an important factor (Henderson, B. W., Bellnier, D. A., Greco, W. R., Sharma, A., Pandey, R. K., Vaughan, L. A., Weishaupt, K. R., Dougherty, T. J., An in vivo Comparative Structure-Activity Relationship for a Congeneric Series of Pyropheophorbide Derivatives as Photosensitizers for Photodynamic Therapy, Cancer Research, 57, 4000–4007, 1997 and references therein; Pandey, R. K., Sumlin, A. B., Potter, W. R., Bellnier, D. A., Henderson, B. W., Constantine, S., Aoudia, M., Rodgers, J. A. J., Smith, K. M., Dougherty, T. J., Alkyl Ether Analogs of Chlorophyll A Derivatives: Synthesis, Photophysical Properties and Photodynamic Efficacy, Photochemistry and Photobiology, 64, 194–204, 1996; Zheng, G., Potter, W. R., Sumlin, A., Dougherty, T. J., Pandey, R. K., Photosensitizers Related to Purpurin-18-N-Alkylimides: A Comparative in vivo Tumoricidal Ability of Ester Versus Amide Functionalities, Bioorg. Med. Chem. Lett., 10, 123–127, 2000; Rungta, A., Zheng, G., Missert, J. R., Potter, W. R., Dougherty, T. J., Pandey, R. K., Purpurinimides as Photosensitizers: Effect of the Presence and Position of the Substituents in the in vivo Photodynamic Efficacy, Bioorg. Med. Chem. Lett., 10, 1463–1466, 2000).

Some attempts have been made to direct photosensitizers to known cellular targets by creating a photosensitizer conjugate, where the other molecule is a ligand that is specific for the target. For example, to improve localization to cell membranes cholesterol (Hombrecher, H. K., Schell, C., Thiem, J. Synthesis and Investigation of Galactopyranosyl-Cholesteryloxy Substituted Porphyrin, Bioorg. Med. Chem. Lett., 6:1199–1202, 1999) and antibody-conjugates have also been prepared to direct photosensitizers to specific tumor antigens (Donald, P. J., Cardiff, R. D., He, D., Kendell, K., Monoclonal Antibody-Porphyrin Conjugate for Head and Neck Cancer; the Possible Magic Bullet, Otolaryng Head Neck Surg., 105:781–787, 1991; Vrouenraets, M. B., Visser, G. W. M., Stewart, F. A., et al., Development of Meta-tetrahydroxyphenylchlorin-monoclonal Antibody Conjugate for Photoimmunotherapy, Cancer Res., 59:1505–1513, 1999). Certain chemotherapeutic agents have also been attached to porphyrin chromophores to increase the lethality of the PDT treatment (Karagianis, G., Reiss, J. A., Marchesini, R., et al., Biophysical and Biological Evaluation of Porphyrin-Bisacridine Conjugates, Anti-Cancer Drug Design 11:205–220, 1996). Certain protein- and microsphere-conjugates were made to improve the pharmacology of the compounds (Bachor, B. S., Shea, C. R., Gillies, R., Hasan, T., Photosensitized Destruction of Human Bladder Carcinoma Cells Treated with Cholrine6-Conjugates Microspheres, Proc. Natl. Acad. Sci., USA 88:1580–1584, 1991). These strategies seldom work well because the pharmacological properties of both compounds are drastically altered (MacDonald, I. J., Dougherty, T. J., Baqsic Principles of Photodynamic Therapy, J. Porphyrins Phthalocyanines, 5:105–129, 2001).

Since oligosaccharides play essential roles in molecular recognition, (Engvall, E., Enzyme Immunoassay ELISA and EMIT, Methods in Enzymology, 70, 419–439, 1980) porphyrins with sugar moieties should not only have good aqueous solubility but also possible specific membrane interaction. In recent years, various glycoconjugated porphyrins have been reported as potential photosensitizers; most of them are based on tetraphenylporphyrin (TPP) analogs (Chen, Y., Jain, R. K., Chandrasedkaran, E. V., Matta, K. L., Use of Sialylated or Sulfated Derivatives and Acrylamide Copolymers of Gal Beta 1,3GalNAc Alpha- and GalNAc Alpha- to Determine the Specificities of Anti-T and Anti-Tn Antibody Levels in Cancer Patients, Glycoconjugate J., 12, 55–62, 1995). However, none of them are known to show any specific cellular target, therefore, so far, no target-based rationally designed PDT agents based on this concept has been reported.

The galectins are a family of animal lectins defined by a highly conserved 15-kDa carbohydrate recognition domain (CRD) showing affinity for β-galactoside (Morgan, J., Potter, W. R., Oseroff, A. R., Comparison of Photodynamic Targets in a Carcinoma Cell Line and its Mitochondrial DNA-Deficient Derivatives, Photochem. Photobiol., 70, 747–757, 1999). Because galectins are involved in the modulation of cell adhesion, cell growth, immune response and angiogenesis, it is clear that changes in their expression might have a critical role in tumor progression. Galectin-1 (Gal-1) is a prototype, dimeric galectin with two identical CRDs, and its expression is known to correlate with the degree of malignancy in rat thyroid cell lines transformed with several cellular or viral oncogenes (MacDonald, I., Morgan, J., Bellnier, D. A., Paszkiewicz, G. M., Whitaker, J. E., Litchfield, D. J., Dougherty T. J., Subcellular Localization Patterns and their Relationship to Photodynamic Activity of Pyropheophorbide-a Derivatives, Photochem. Photobiol., 70, 789–997, 1999). Gal-1 mRNA levels increase 20 fold in low tumorigenic and up to 100-fold in high tumorigenic cells. These observations are consistent with those observed in human tumors (Kozyrev, A. N., Suresh, V., Das, S., Senge, M. O., Shibata, M., Dougherty, T. J., Pandey, R. K., Syntheses and Spectroscopic Studies of Novel Chlorins with Fused Quinoxaline or Benzimadazole Ring Systems and the Related Dimers with Extended Conjugation, Tetrahedron, 56, 3353–3364, 2000).

Furthermore, Gal-1 null mutant mice are found to be relatively healthy (Chiariotti, L., Salvatore, P., Benvenuto, G., Bruni, C. B., Control of Galectin Gene Expression, Biochimie, 81, 381–388, 1999; Salvatore, P., Benvenuto, G., Pero, R., Lembo, F., Bruni, C. B. and Chiaritti, L., Galectin-1 Gene Expression and Methylation State in Human T Leukemia Cell Lines, International Journal of Oncology, 17:1015–1018, 2000). Galectin-1 and galectin-3 are expressed in many epithelial tumors such as colon, thyroid, and breast carcinoma. However, there are still controversies whether galectin-3 promotes the metastatic potential and correlates with the poorly differentiated morphology or not. For example, the expression of galectin-3 inversely correlated with metastatic potential in breast and thyroid carcinoma, while in another study over-expression of galectin-3 conferred an increased metastatic potential to low metastatic cells in mouse melanoma and fibrosarcoma cells. It has recently been shown that the level of galectin expression increases and correlates with the neoplastic progression of colon carcinoma (Chiariotti, L., Salvatore, P., Benvenuto, G., Bruni, C. B., Control of Galectin Gene Expression, Biochimie, 81, 381–388, 1999; Salvatore, P., Benvenuto, G., Pero, R, Lembo, F., Bruni, C. B. and Chiaritti, L., Galectin-1 Gene Expression and Methylation State in Human T Leukemia Cell Lines, International Journal of Oncology, 17:1015–1018, 2000).

For the development of more effective cancer therapies it is important to have a better understanding of the molecular mechanisms that control invasion and metastases. In this regard, pathological interactions between cancer cells and the basement membrane (BM), a specialized extracellular matrix, have been extensively investigated (Castronovo, V., Laminin Receptors and Laminin-Bindign Proteins During Tumor Invasion and Metastasis, Invasion Metastasis, 13:1–30, 1993). The BM constitutes a barrier that cancer cells must cross several times during dissemination (Liotta, L. A., Tumor Invasion and Metastasis-Role of the Extracellular Matrix: Rhoads Memorial Award Lecture, Cancer Res., 46:1–7, 1986). Interactions between cancer cells and laminin, the main BM glycoprotein, are critical for successful invasion of these barriers. Several cell surface molecules have been described as laminin-binding proteins. Among these a few members of the galectin family also exhibit an altered pattern of expression in invasive and metastatic cancer cells (Castronovo, V., Laminin Receptors and Laminin-Bindign Proteins During Tumor Invasion and Metastasis, Invasion Metastasis, 13:1–30, 1993; Andre, S., Kojima, S., Yamazaki, N., Fink, S., Kaltner, H., Kaysev, K., Gabius, H. J., Galectin-1 and -3 and their Ligands in Tumor Biology, J. Cancer Res Clin Oncol., 125:461–474, 1999). Gal-1 and Gal-3 the two galactose-specific lectins bind laminin through its poly-N-acetyl-lactosamine residue. A high expression of Gal-1 and decreased expression of Gal-3 was found in uterine adenocarcinoma (Van Den Brule, F. A., Berchuck, A., Bast, R. C., Deprez, M., Liu, F. T., Cooper, D. N. W., Pieters, C., Bosel, M. E., and Castronovo, V., Expression of the 67-kD Laminin Receptor, Galectin-1and Galectin-3 in Advanced Human Uterine Adenocarcinoma, Human Pathology, 27:1185–1191, 1996).

Analyses of the carbohydrate binding sites in Gal-1 and Gal-3 show that both galectins have a pronounced specificity for the Gal(β1–4)- and Gal(β1–3)GlcNAc sequences with no apparent affinity for GlcNAc residues. The binding specificity for Fal moiety is due to hydrogen bond interactions between its C4-hydroxy group and His 44, Asn 46 and Arg 48 residues that are conserved in all galectins. The van der Waals contact of Trp 68 with the Gal moiety as well as the hydrogen bonding of C6-hydroxy group to Gal-1 also contribute to binding (Rini, J. M., Lectin Structure, Annu. Rev. Biophys. Biomol. Struct. 24, 551–577, 1995).

Since our objective has included development of target specific photosensitizers as therapeutic agents for photodynamic therapy, we were interested in establishing a general synthetic route for the preparation of β-galactoside based long wavelength absorbing photosensitizers as Gal-1 recognizing agents. Our study was aimed at determining the effect of the presence of carbohydrate moieties on tumor selectivity and to explore the viability of this approach in converting an inactive compound with the required photophysical properties into an active therapeutic drug.

BRIEF DESCRIPTION OF THE INVENTION

Our invention deals with:

(i) An efficient approach for the preparation of β-galactose conjugated photosensitizers with required photophysical properties.

(ii) The galectin-1 (Gal-1) inhibition binding affinity (by ELISA assay) of the conjugates with the parent molecule.

(iii) The comparative in vitro photosensitizing efficacy of the conjugates with the parent molecule.

The invention includes compounds of the invention having the following generic formula:

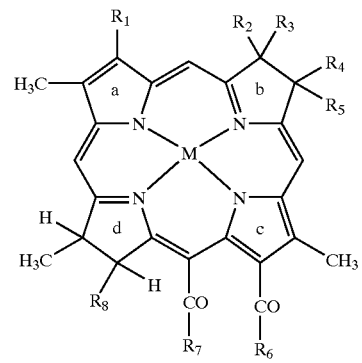

where $R_1$ is lower alkyl, vinyl, aryl, alkyl ether, aryl, lower carboxy, or —CH(OR$_9$)CH$_3$ where $R_9$ is alkyl of 1 to about 20 carbon atoms, a cyclic containing substituent containing 1 to about 20 carbon atoms connected to the a ring through a carbon-carbon or —O— bond; $R_2$ and $R_5$ are independently hydrogen or lower alkyl, $R_3$ and $R_4$ are independently —H, lower alkyl, or —OR$_{10}$, where $R_{10}$ is H or lower alkyl, or $R_3$ and $R_4$, together form a covalent bond; $R_6$ and $R_7$ taken together are =NR$_{11}$ or are independently —OR$_{11}$, where $R_{11}$ is independently —H, alkyl of 1 to about 20 carbon atoms, a cyclic containing substituent containing 1 to about 20 carbon atoms, an amide group or a mono or polysaccharide containing substituent connected through an intermediate group containing one or more of a saturated or unsaturated lower alkylene group, a saturated or unsaturated heterocylic or hydrocarbon five or six membered ring, an ether linkage, an amide linkage or an ester group; $R_8$ is —CH$_2$CH$_2$COR$_{12}$ where $R_{12}$ is an amino acid residue, —NHR$_{13}$ or —OR$_{14}$ where $R_{13}$ is hydrogen, alkyl of 1 to about 20 carbon atoms, or a substituent containing a mono or polysaccharide and $R_{14}$ is hydrogen, or alkyl of 1 to about 20 carbon atoms, where lower alkyl includes alkyl and alkylene groups of 1 to 5 carbon atoms and alkyl includes linear, branched and cyclic unsubstituted alkyl and linear, branched and cyclic alkyl and alkylene groups substituted with hydroxy, carboxy, alkyl, vinyl, amino, amido, keto, heterocyclic, mono and polysaccharide and amino acid groups; provided that the compound contains at least one mono or polysaccharide group that will combine with galectin-1. and M is a chelated metal or is two hydrogens bound to the unsaturated nitrogens in the a and c rings.

The invention especially includes such compounds containing at least one galactose or lactose saccharide group and M is two hydrogens as above described.

In the most preferred compounds $R_6$ and $R_7$ together are =$NR_{11}$ where $R_{11}$ contains a mono or polysaccharide moiety.

The invention further includes a method for treating cancer cells by contacting the cells with the above compound and exposing the cells to light.

BRIEF DESCRIPTION OF THE DRAWINGS

FIG. 1 shows chemical structures of purpurinimide 1a and corresponding galactose and lactose conjugates 2a–4a.

DETAILED DESCRIPTION OF THE INVENTION

Figure 1:
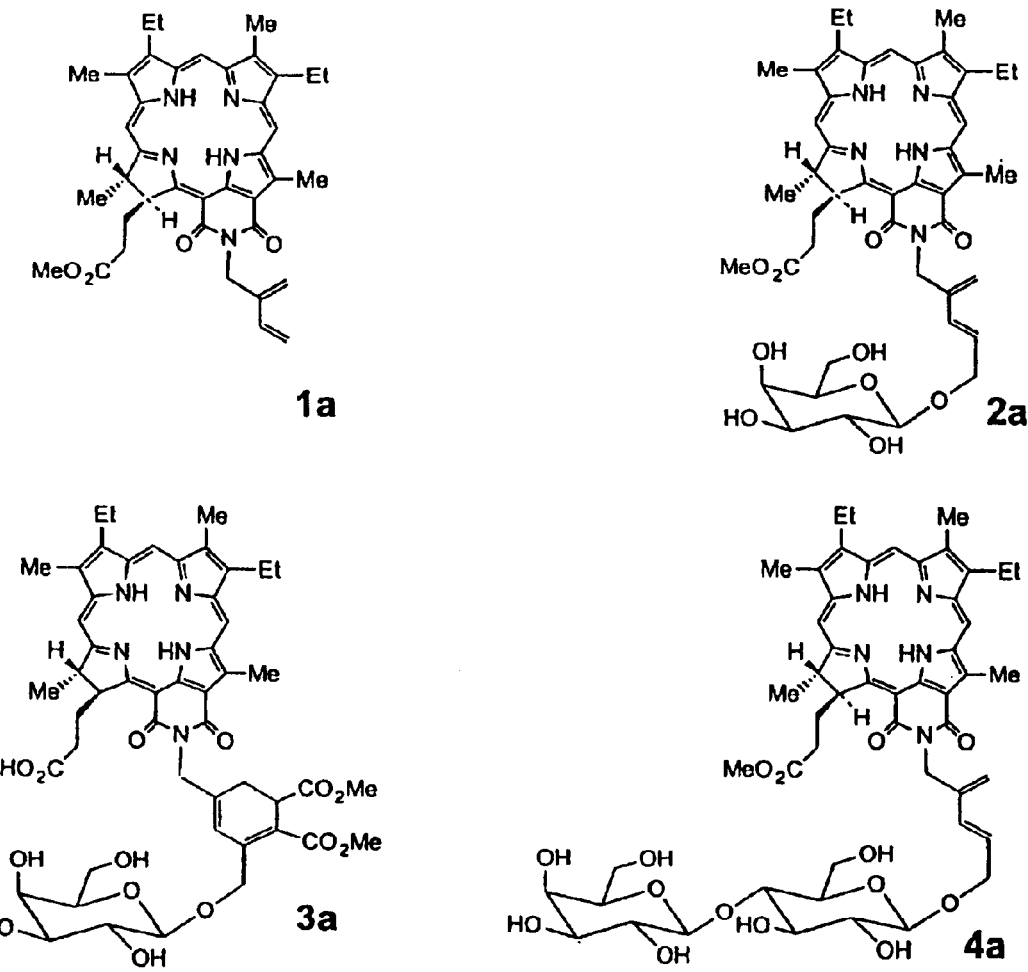

The structures of compounds 2a, 3a and 4a of FIG. 1 are built from the crystal structure of benzimidazo(2,1-n) purpurin-18 13$^1$-imino-13$^2$-imide methyl ester (Kozyrev. A. N., Suresh, V., Das, S., Senge, M. O., Shibata, M., Dougherty T. J., Pandey, R. K., Syntheses and Spectroscopic Studies of Novel Chlorins with Fused Quinoxaline or Benzimadazole Ring Systems and the Related Dimers with Extended Conjugation, Tetrahedron, 56, 3353–3364, 2000). Appropriate modifications were performed with the SYBYL modeling program version 6.6 (Tripos Inc., St. Louis, Mo.)

using standard geometry and the SYBYL fragment library. The extended conformation was assumed for the linker region. The geometry of each compound was fully optimized with a semi-empirical molecular orbital method, AM1, with the SPARTAN (Wavefunction Inc, Irvine, Calif.) program.

The binding specificity of the chlorin-carbohydrate conjugates for Gal moiety is due to the ability of these compounds to bind to the cellular target, and was examined by molecular modeling of the galectin chlorin-carbohydrate conjugate complexes. Since the high resolution crystal structures of many galectins in free and in the presence of galactose, galactosamine, lactose, and N-acetyl-lactosamine are available (Protein Data Bank code, 1BKZ, 2GAL, 3GAL (3AIK), 4GAL, 5GAL), (Leonidas, D. D., Vatzaki, E. H., Vorum, H., Celis, J. E., Madsen, P., Acharya, K. R., Structural Basis for the Recognition of Carbohydrates by Human Galectin-7, Biochemistry, 37, 13930–13940, 1998) we utilized this system as our template. It should be noted that essentially all galectins, including bovine galectin-1 and human galectin 3 and galectin-7, share the same carbohydrate recognition domain (CRD) although there are some differences in the structural details of the binding site. The aim of this modeling study was to obtain a rationale for the positioning of the chlorin moiety that does not interfere with the carbohydrate recognition by Gal-1 and Gal-3. The optimized structures of compounds 2a and 3a are placed into the binding site by using crystal structure of the complexes, 2GAL. The six galactose ring atoms were used for the superposition of the galactose with the galactose moiety of the compounds 2a and 3a. Similarly, the crystal structure 4GAL was used to place the compound 4a in to the binding site of Gal-7 with the six galactose ring atoms as a guide.

Figure 12A:
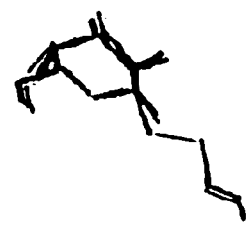
FIGS. 12a, 12b and 12c show superposition of the galactose ring atoms between the crystal structure of galactose/lactose with the AMI optimized geometries of compound 2 (12a) 3 (12b) and 4 (12c) respectively. The crystal structure is drawn in bold lines while the model compounds are drawn light lines.
Figure 12B:
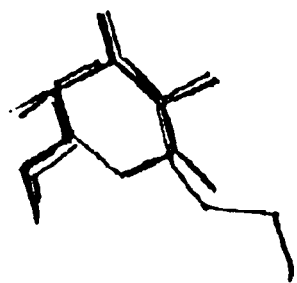
Figure 12C:
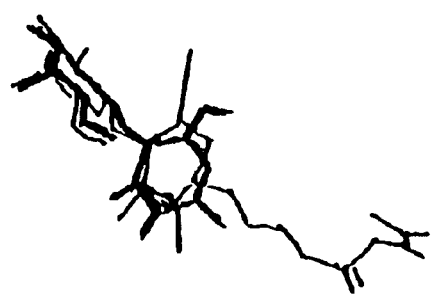
Figure 13A:
FIGS. 13a and 13b show an overview of the structures of galectin-7 and compound 2; and galectin-7 (13a) and compound 4 (13b), respectively. The chlorin attached to the carbohydrate is shown protruding from the structure while the galectin-7 is shown with the atomic details and schematic presentation of the secondary structure. It is clear from this figure that the chlorin moiety for all chlorin carbohydrate is pointing out towards solvents thus, not interfering with the carbohydrate-galectin recognition.
Figure 13B:
Figure 14A:
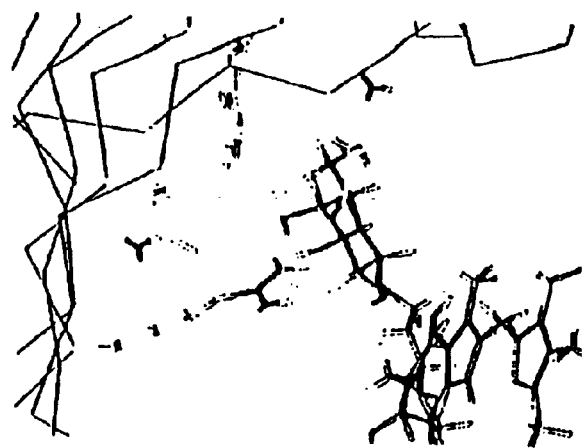
FIGS. 14a and 14b show close-up views of the carbohydrate binding site of the galectin-chlorin-carbohydrate conjugate complexes for the compound 2 (14a) and compound 4 (14b) respectively. The chlorin-carbohydrate conjugates are shown in heavy stick figures while the suggested binding residues are shown with light stick and residue labels. The protein back bone is shown in a carbon-a trace while the side chain of the residues that are within 5 Å from the chlorin-carbohydrate conjugate atoms are drawn with thin lines.
Figure 14B:
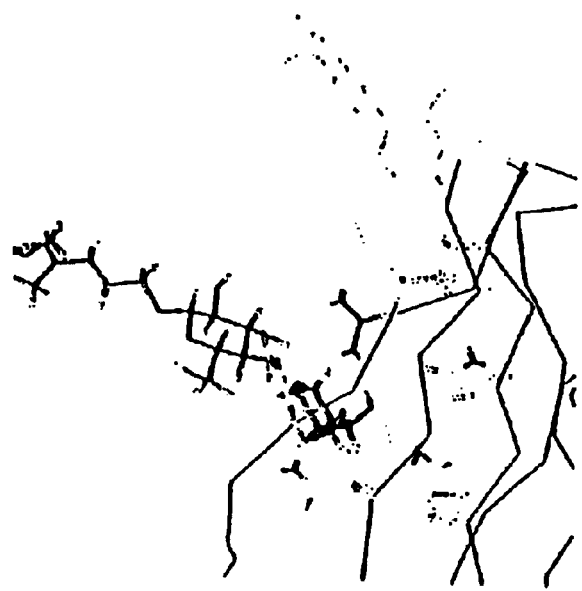

The superposition operations resulted in good fit for all the compounds with the root mean square deviation values ranging from 0.03 to 0.04 Å (see FIGS. 12a–12c). The resulting structures of the complex clearly indicated that the chlorin moiety is far from the galactose binding site. Thus they should not interfere with the recognition of the carbohydrate moiety by galectin-1. The overall view of the complexes for the compound 2a and 4a are shown in FIGS. 13a and 13b while the close-up views of the binding site are shown in FIGS. 14a and 14b.

To our knowledge this is the first report that illustrates an efficient approach for the synthesis of Gal-1 recognized chlorin-based photosensitizers for photodynamic therapy. These compounds with significant Gal-1 inhibition binding affinity ($I_{50}$) appear to localize to the cell surface. An increase in the Gal-1 inhibition ($I_{50}$) as well as in vitro PDT efficacy was observed by replacing the galactose with a Gal(β1–4)-Glc(lactose) moiety. Thus, this approach has great potential in converting a non-active compound with the required photophysical characteristics into an effective photosensitizer. Compared to the β-galactoside conjugate 2a, photosensitizer 3a containing a linker with a six membered ring system produced enhanced Gal-1 inhibition. The molecular modeling results suggest that the six membered ring of the linker is diminishes the flexibility of the linker as well as mimics the glucose moiety of βGal(1–4)-Glc. However, to our surprise, while this modification produced a significant increase in galectin binding affinity (photosensitizer 3a), it did not enhance the PDT efficacy. Replacing galactose with a lactose moiety (photosensitizer 4a), however, produced a significant increase in Gal-1 inhibition as well as in vitro photosensitizing efficacy.

Similar results (FIG. 2) are obtained using human galectin-3 carbohydrate recognition domain complexed with N-acetyl lactosamine (Protein Data Bank Code 3AIK, Seetharaman et al, 1998) in the model as a template to model galectin-3 chlorin-carbohydrate conjugates complex. It should again be noted that the aim of this modeling study was to obtain a rationale for the positioning of the chlorin moiety that does not interfere with the carbohydrate recognition by galectin-3 (both Gal-1 and Gal-3 are known to have the same carbohydrate recognition domain). The optimized structure of chlorin-carbohydrate conjugate was placed into the binding site. The six ring atoms as well as C6 and O6 atoms of galactose were used for the superposition of the galactose portion of N-acetyllactosamine with the galactose moiety of the conjugated photosensitizer. No attempt was made to optimize the orientation of the chlorin or linker regions towards galectin-3.

Figure 2:
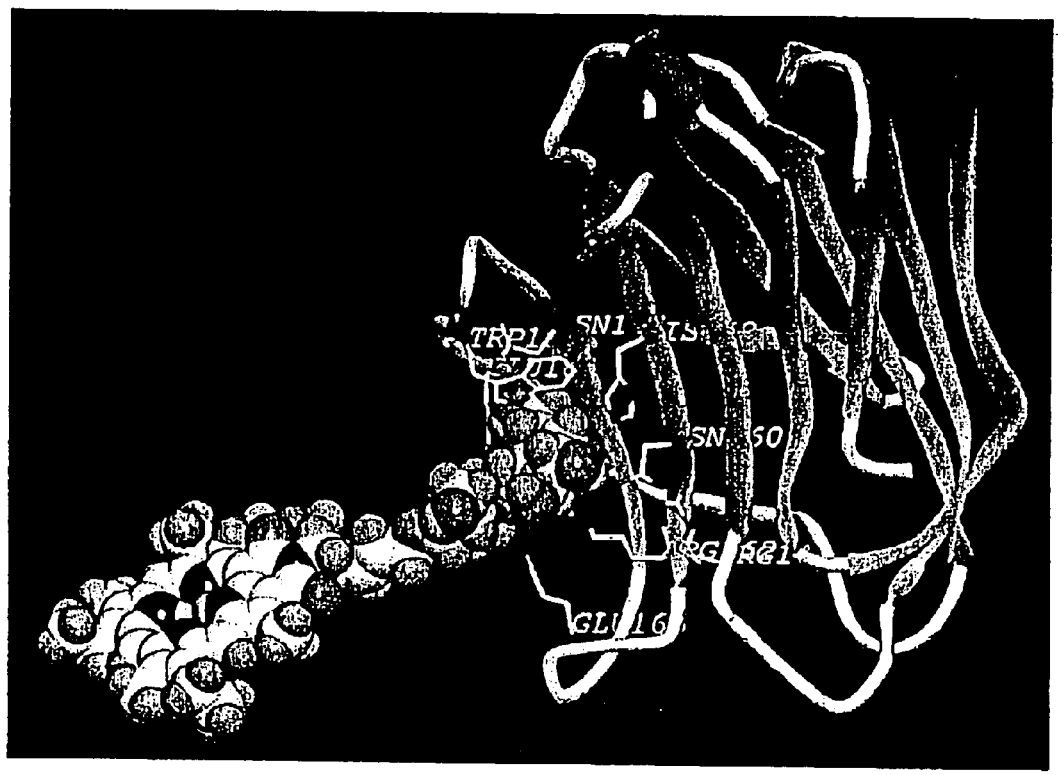
FIG. 2 shows a stereochemical model of human galectin-3 and its purpurinimide-lactose conjugate 4a complex. It is clear that the chlorin moiety is not interfering with the carbohydrate-galectin recognition.

An elevated expression of galectin-3 in cancer cells has been reported. Thus, the crystal structure of the galectin-3 and N-acetyllactoseamine complex was used as the model to examine the orientation of photosensitizer upon formation of the complex (FIG. 2). The superposition operation resulted in good fit with the root mean square deviation value of 0.10 Å. The resulting structures of the complex clearly indicated that the chlorin moiety is far from the galactose binding site thus should not interfere with the recognition of the carbohydrate moiety by galectin-3. Since the aim of this study was to examine the feasibility of the chlorin-carbohydrate conjugate binding to galectin-3, only a limited conformational flexibility was examined for the ligand binding. The carbohydrate recognition model of lactose-chlorin conjugate by galactin-3 is identical to what is found in the crystal structure of N-acetyllactoseamine galectin-3 complex. In addition to van der Waals contact of galactose moiety with Trp181, several hydrogen bonds were formed between galactose moiety and galectin-3 including O4-His158, O4-Asn160, O4-Arg162, O5-Arg162, O6-Asn172, O6-184.

In our approach, for retaining the binding affinity of the carbohydrate conjugate at the target site, we decided to link a photosensitizer with a spacer at position-1 of the β-galactose. For our study, purpurin-18 methyl ester 1 (Smith, K. M. (Ed). Porphyrins and Metalloporphyrins, Elsevier Scientific Publication, Amsterdam 1975) was selected as a starting material due to its many advantages over TPP and other types of porphyrins: (a) its ready availability from chlorophyll a (b) its strong absorption near 700 nm, thus, the ability to treat deeply seated tumors; (c) its high singlet oxygen yield (55%), a key cytotoxic agent for PDT; (d) the presence of the vinyl, propionic acid side chain and the fused anhydride ring systems that can be modified easily, thus, avoiding multistep total syntheses. On the basis of molecular modeling, appropriate imide-based spacers can be introduced between the photosensitizer and the carbohydrate moiety through the fused anhydride ring system.

In order to construct the desired β-galactose conjugated photosensitizers, we extended our recent approach developed for the preparation of chlorin-diene 1a via ruthenium catalyzed enyne metathesis (Zheng, G., Dougherty, T. J., Pandey, R. K., Novel Chlorin-Diene Building Block by Enyne Metathesis: Synthesis of Chlorin-Fullerene Dyads, Chem. Commun. 2469–2470, 1999). For our initial studies, purpurin-18 methyl ester 1 on hydrogenation over Pd/carbon was converted into mesopurpurin-18 methyl ester 2 in 90% yield. Reaction of 2 with propargylamine in refluxing benzene for 12 h produced the corresponding propargylimide derivative 3 in 80% yield, and was used as the alkyne substrate for yne-ene cross metathesis. As for the alkene component, acetylated β-D-1-O-allyl-galacto-pyranoside 6 was prepared from β-D-galactose penta-acetate 5 by $BF_3$- etherate induced glycosylation (Magnusson, G., Noori, G., Dahman, J., Frejd, T., Lave, T., BF3-Etherate Induced Formation of 2,2,2-Trichloroethyl-Glycopyranosides Selective Visualization of Carbohydrate Derivatives on TLC Plates, Acta, Chemica. Scandinavica B, 35, 213–21, 1981). Compounds 4 (1a) and 6 were then introduced to yne-ene cross metathesis reaction by treating the Grubbs' ruthenium catalyst in $CH_2Cl_2$ solution at room temperature for 48 hours. The galactopyranose-chlorin conjugate 7 was obtained in 40% yield as the diastereomeric mixture, due to the incorporation of the E/Z mixtures of the carbohydrate-substituted 1,3-diene. In order to determine the effect of the rigidity of the spacer to the Gal-1 binding affinity and PDT efficacy, compound 7 on refluxing with dimethyl acetylenedicarboxylate (DMAD) in toluene afforded the corresponding Diels-Alder adduct 9. As expected, deacetylation of diene 7 by $NaOMe/MeOH$—$CH_2Cl_2$ produced the expected conjugate 8 (2a). The removal of the acetyl groups in 9 under similar reaction conditions produced chlorin 10 (3a) as the major product and the unexpected chlorin 11 as a minor component (Scheme 1). A possible mechanism for the formation of these compounds via the base-catalyzed rearrangement is illustrated in Scheme 2. Following a similar approach as discussed for the preparation of conjugate 8, diene 4 was reacted with 13 and the related photosensitizer containing a lactose moiety 15 (4a) was obtained in 30% yield (Scheme 1). $^1H$ NMR and mass spectrometry/elemental analyses confirmed the structures of all new compounds.

The following examples give specific procedures for preparation of conjugates. Mesopurpurin-18-N-propargylimide Methyl Ester (3). A mixture of 475 mg (0.82 mmol) of mesopurpurin-18 methyl ester 2, and 3 g (55 mmol) of propargylamine was dissolved in 40 ml of benzene, and the mixture refluxed under an argon atmosphere overnight. After cooling to room temperature, solvent and excess propargylamine were removed. The crude product was purified by silica column chromatography with 2% methanol in dichloromethane. Crystallization of the product with dichloromethane and hexanes afforded 425 mg (0.69 mmol) of the title compound as purple solid, yield 85%. UV-vis in $CH_2Cl_2$, $\lambda_{max}$ (nm, $\epsilon$): 692 (4.50×10$^4$), 543 (2.05×10$^4$), 506 (7.66×10$^3$), 413 (1.40×10$^5$), 360 (5.22× 10$^4$); MS (FAB) found: m/z 618.0 (100, M$^{++1}$); Anal. Calcd for $C_{37}H_{39}N_5O_4 \cdot \frac{1}{2}H_2O$: C, 70.89; H, 6.44; N, 11.18. Found: C, 71.25; H, 6.41; N, 10.91. $^1HNMR$ (400 MHz, 5.0 mg/mL CDCl$_3$, δ ppm): 9.56, 9.17 and 8.50 (each s, 1H, 5-H, 10-H and 20-H); 5.40 (dd, J=8.9 and 2.7 Hz, 1H, 17-H); 5.29 (dd, J=6.5 and 2.3 Hz, 2H, N—CH$_2$); 4.35 (q, J=7.4 Hz, 1H, 18-H); 3.81, 3.59, 3.24 and 3.17 (each s, 3H, 2-, 7-, 12-CH$_3$, and CO$_2$CH$_3$); 3.75 and 3.63 (each q, J=7.9 Hz, 2H, 3- and 8-CH$_2$CH$_3$); 2.74 (m, 1H, 1×17CH$_2$CH$_2$CO$_2$CH$_3$); 2.43 (m, 2H, 1×17CH$_2$CH$_2$CO$_2$CH$_3$ and 1×17 CH$_2$CH$_2$CO$_2$CH$_3$); 2.32 (t, J=2.2 Hz, 1H, C≡CH); 2.01 (m, 1H, 1×17CH$_2$CH$_2$CO$_2$CH$_3$); 1.76 (d, J=7.2 Hz, 3H, 18-CH$_3$); 1.71 and 1.67 (each t, J=8.0 Hz, 3H, 3-CH$_2$CH$_3$ and 8-CH$_2$CH$_3$); 0.19 and −0.01 (each br s, 1H, 2N—H). Per-O-acetylated 1-O-allyl-β-D-galacto-pyranose (6): To a cooled solution of 5.0 g (12.8 mmol) of per-acetylated galactose and 1.05 ml (15.4 mmol) allyl alcohol in 20 ml dry dichloromethane, 8.0 ml boron trifluoride etherate (63 mmol) was added dropwise. The ice bath was removed after 0.5 h, and the reaction was allowed to warm to room temperature until the starting material had been consumed (monitored by TLC). Then the reaction mixture was poured into 300 ml aqueous sat. sodium bicarbonate solution. It was extracted with dichloromethane and washed with water. Drying (Na$_2$SO$_4$) and evaporation of the dichloromethane layer gave a crude residue, which was chromatographed on silica column with 30% ethyl acetate in cyclohexane to afford 3.2 g (8 mmol) of the title compound, yield 60%. MS (FAB) found: m/z 331.3 (M-5703 (O-allyl)). $^1H$ NMR (400 MHz, 5.0 mg/mL CDCl$_3$, δ ppm): 5.83 (m, 1H, OCH$_2$CH═CH$_2$); 5.33 (d, J=3.5 Hz, 1H, 4-H); 5.27–5.12 (m, 3H, OCH$_2$CH═CH$_2$ and 2-H); 4.97 (dd,J=10.0 and 3.0 Hz, 1H, 3-H); 4.50 (d, J=8.1 Hz, 1H, 1-H); 4.32 (dd, J=13.3 and 4.9 Hz, 1H, 1×6-H); 4.17–4.05 (m, 3H, 1×6-H and OCH$_2$CH═CH$_2$); 3.88 (t, J=6.6 Hz, 1H, 5-H); 2.12, 2.03, 2.02 and 1.95 (each s, 3H, 4×COCH$_3$).

Per-acetylated 1-O-allyl-β-D-galactopyranosyl-(14)-β-D-glucopyranose (13). Following the methodology as described above, the title compound was obtained from β-D-lactose octaacetate and allyl alcohol with boron trifluoride etherate in 50% yield. MS (FAB) found; m/z 676.5 (100, M). $^1H$ NMR (400 MHz, 5.0 mg/mL CDCl$_3$, δ ppm): 5.84 (m, 1H, OCH$_2$CH═CH$_2$); 5.50–3.59 (each m, total 18H, 14-Lac-H and 4H from OCH$_2$CH═CH$_2$); 2.15 and 2.12 (each s, 3H, 2×COCH$_3$); 2.06 (s, 6H, 2×COCH$_3$); 2.04 (s, 9H, 3×COCH$_3$); 1.96 (s, 3H, COCH$_3$).

Mesopurpurin-18-N-methyl-(2'-butadiene)imide (4). A mixture of 300 mg (0.48 mmol) of propargylimide 3 and 40 mg Grubbs's catalyst (bis(tricyclohexylphosphine)benzylidine ruthenium (IV)) (10 mol %) were dissolved in 40 ml of dry dichloromethane. The flask was equipped with a balloon filled with ethylene gas. The reaction mixture was stirred under ethylene atmosphere for 48 h. After evaporating of solvent, the crude was separated by silica column with 1.5% methanol in dichloromethane. The title compound was obtained in 30% yield. On the basis of the starting material recovered, the yield was quantitative. UV-vis in $CH_2Cl_2$ $\lambda_{max}$ (m, $\epsilon$): 695 (4.5×10$^4$), 640 (9.1×10$^3$), 545 (2.2×10$^4$), 505 (7.8×10$^3$), 480 (4.5×10$^3$), 415 (1.4×10$^5$), 360 (5.4×10$^4$); MS (FAB) found: m/z 646.6 (100, M$^{++1}$); $^1H$ NMR (400 MHz, 5.0 mg/mL CDCl$_3$, δ ppm): 9.60, 9.20 8.51 (each s, 1H, 5-H, 10-H and 20-H); 6.69 (dd, J=17.8 and 11.1 Hz, 1H, 3'-H); 5.63 (d, J=17.7 Hz, 1H, trans-4'-H); 5.40 (dd, J=9.0 and 2.5 Hz, 1H, 17-H); 5.31 (d, J=11.0 Hz, 1H, cis-4'-H); 5.31 (s, 2H, N—CH$_2$); 5.21 (d, J=15.2 Hz, 2H, 2×1'-H); 4.33 (q, J=7.5 Hz, 1H, 18-H); 3.82, 3.55, 3.25 and 3.18 (each s, 3H, 2-, 7-, 12-CH$_3$ and CO$_2$CH$_3$); 3.76 and 3.64 (each q, J=7.7 Hz, 2H, 3- and 8-CH$_2$CH$_3$); 2.67 (m, 1H, 1×17CH$_2$CH$_2$CO$_2$CH$_3$); 2.38 (m, 2H, 1×17CH$_2$CH$_2$CO$_2$CH$_3$ and 1×17CH$_2$CH$_2$CO$_2$CH$_3$); 2.00 (m, 1H, 1×17CH$_2$CH$_2$CO$_2$CH$_3$); 1.76 (d, J=7.2 Hz, 3H, 18-CH$_3$); 1.71 and 1.67 (each t, J=8.0 Hz, 3H, 3-CH$_2$CH$_3$ and 8-CH$_2$CH$_3$); 0.14 and −0.07 (each br s, 1H, 2N—H).

Per-acetylated Galactose-Chlorin conjugate joined with 2',4'-diene linkage (7). To a solution of 150 mg (0.24 mmol) of propargylimide 3 and 350 mg (0.90 mmol) of O-allyl-sugar 6 in 10 ml of dichloromethane, 25 mg (0.03 mmol) of Grubbs's catalyst was added. The reaction mixture was stirred under argon for 24 h. It was kept stirring for 24 h after adding another 25 mg (0.03 mmol) of catalyst. After evaporating the solvent, the crude residue was purified by silica plate preparative chromatography, eluting with 2% methanol in dichloromethane. The title compound was obtained in 30% yield (70 mg). MS (FAB) found: m/z 1006.9 (100, M$^{++1}$); Anal. Calcd for $C_{54}H_{63}N_5O_{14} \cdot H_2O$: C, 63.31; H, 6.40; N, 6.84. Found: C, 62.92: H, 6.20; N, 6.48. $^1H$ NMR (400 MHz, 5.0 mg/mL CDCl$_3$, δ ppm) showing a diastereomeric mixture: 9.61 and 9.59 (each s, total 2H, 1×meso-H); 9.20 and 8.50 (each s, 2H, 2×meso-H); 6.65–3.90 (each m, total 30H, 14 sugar H, 2×17-H, 2×18-H, 12H for (2'-butadiene)); 3.82 and 3.81 (each s, total 6H, 2×CH$_3$); 3.76 and 3.65 (each q, J=7.6 Hz, total 8H, 2×3- and 8-CH$_2$CH$_3$);

3.71 and 3.55 (each m, total 4H, 2×4'-CH$_2$O); 3.57 and 3.54 (each s, total 6H, 2×CH$_3$); 3.25 and 3.18 (each s, 6H, 4×CH$_3$); 2.67 (m, 2H, 2×17CH$_2$CH$_2$CO$_2$CH$_3$); 2.37 (m, 4H, 2×17CH$_2$CH$_2$CH$_3$ and 2×17CH$_2$CH$_2$CO$_2$CH$_3$); 2.22–19.2 (m, total 26H, 2×17CH$_2$CH$_2$CO$_2$CH$_3$ and 8×COCH$_3$); 1.76 (d, J=7.2 Hz, 6H, 2×18-CH$_3$); 1.71 and 1.68 (each t, J=8.0 Hz, 6H, 2×3-CH$_2$CH$_3$ and 8-CH$_2$CH$_3$); 0.18, 0.09, −0.04 and −0.10 (each br s, total 4H, 4×N—H).

Galactose-Chlorin conjugate Joined with diene linkage (8, 2a): To a solution of 40 mg (0.04 mmol) of 7 in 20 ml of dichloromethane, 200 μl of 1M NaOMe in MeOH was added, and the reaction mixture was stirred under argon for 1 h. After the standard work-up, the residue was separated by silica plate chromatography with 8% MeOH/CH$_2$CL$_2$. The title compound was obtained in 50% yield (17 mg). WV-vis in CH$_2$Cl$_2$, $\lambda_{max}$ (nm, ε): 695 (4.5×10$^4$), 640 (8.9×10$^3$), 545 (2.2×10$^4$), 505 (7.8×10$^3$), 480 (4.5×10$^3$), 415 (1.4×10$^5$), 360 (5.4×10$^4$); MS (FAB) found: m/z 839.1 (100, M$^+$+1); $^1$H NMR (400 MHz, 5.0 mg/mL CDCl$_3$, δ ppm) showing a diastereomeric mixture in 4:1 ratio: 9.35, 9.14, 9.08, 9.02 and 8.46 (each s, total 6H, 2×5-, 10- and 20-H); 6.67–3.55 (each m, total 34H, 14 sugar H, 2×17-H, 2×18-H, 16H for linker-H); 3.51, 3.46, 3.22 and 2.96 (each s, 6H, 2×2-, 7-, 12-CH$_3$ and 2×CO$_2$CH$_3$); 3.31 and 3.04 (each m, 4H, 2×3- and 8-CH$_2$CH$_3$); 2.66 (m, 2H, 2×17CH$_2$CH$_2$CO$_2$CH$_3$); 2.36 (m, 4H, 2×17CH$_2$CH$_2$CO$_2$CH$_3$ and 2×17CH$_2$CH$_2$CO$_2$CH$_3$); 1.95 (m, total 2H, 2×17CH$_2$CH$_2$CO$_2$CH$_3$); 1.76 (d, J=7.6 Hz, 6H, 2×18-CH$_3$); 1.68 and 1.48 (each t, J=7.3 Hz, 6H, 2×3- and 8-CH$_2$CH$_3$); −0.12 (br s, total 4H, 4×N—H).

Per-acetylated Galactose-Chlorin conjugate joined with 1,4-cyclohexadiene linkage (9): To a solution of 160 mg (0.16 mmol) of 7 in 20 ml of toluene, 1.0 ml dimethylacetylene dicarboxylate (DMAD) was added. The reaction mixture was refluxed under argon for 3 h. After removing solvent under high vacuum (for removing DMAD), the residue was purified by silica column chromatography, eluting with 2% MeOH/CH$_2$Cl$_2$ to afford 60 mg (0.05 mmol) of the title compound in 33% yield. MS (FAB) found: m/z 1148.6 (100, M$^+$+1); $^1$H NMR (400 MHz, 5.0 mg/mL CDCl$_3$, δ ppm) showing a diastereomeric mixture:

Galactose-Chlorin conjugate joined with 1,3-cyclohexadiene linkage (10, 3a): To a solution of 40 mg (0.035 mmol) of 9 in 20 ml of dichloromethane, 250 μl of 1M NaOMe in MeOH was added, the reaction mixture was stirred under argon for 1 h. After the standard work-up, the residue was separated by silica plate chromatography, eluting with 8% MeOH/CH$_2$CL$_2$ and the title compound was obtained in 44% yield (15 mg) along with 7 mg (0.009 mmol) of 11 in 25% yield. MS (FAB) found: m/z 980.9 (100, M$^+$+1); $^1$H NMR (400 MHz, 5.0 mg/mL CDCl$_3$, δ ppm) showing a diastereomeric mixture: 9.53 (s, 2H, 2×10-H); 9.15 (s, 2H, 2×5-H); 8.46 (s, 2H, 2×20-H); 7.49 and 7.46 (each s, total 2H, 2×13$^5$-H); 6.29 and 6.04 (each s, total 2H, 2×13$^8$-H); 5.30 (m, 2H, 2×17-H); 5.14 (m, 2H, 2×13$^3$-H); 4.98 (m, 2H, 2×13$^3$-H); 4.29 (m, 2H, 2×18-H); 4.18 (m, 2H, 2×Gal-H); 4.04 and 3.99 (each s, total 2H, 2×13$^{10}$-H); 3.85 (m, 4H, 4×Gal-H); 3.77 (s, 6H, 2×12-CH$_3$); 3.75 (m, 4H, 2×3-CH$_2$CH$_3$); 3.70 (m, 4H, 4×Gal-H); 3.63 (m, 2H, 2×Gal-H); 3.60 (m, 4H, 2×8-CH$_2$CH$_3$); 3.53 (s, 6H, 2×17$^3$-CO$_2$CH$_3$); 3.43 and 3.38 (each m, 4H, 4×13$^9$-H); 3.35 (m, 2H, 2×13$^{10}$-H); 3.21 (s, 6H, 2×2-CH$_3$); 3.13 (s, 6H, 2×7-CH$_3$); 2.64 (m, 2H, 2×17$^1$-H); 2.61 (s, 6H, 2×13$^7$-CO$_2$CH$_3$); 2.33 (m, 4H, 2×17$^1$-H and 2×17$^2$-H); 2.15 (s, 6H, 2×13$^8$-CO$_2$CH$_3$); 1.93 (m, 2H, 2×17$^2$-H); 1.74 (d, 6H, 2×18-CH$_3$); 1.68 (t, 6H, 2×3-CH$_2$CH$_3$); 1.65 (t, 6H, 2×8-CH$_2$CH$_3$); 0.17 and −0.12 (each br s, 2H, 4×NH). Mesopurpurin-18-N-1'-(5-methyl-3,4-dicarboxylate methyl ester)phenyl-methyl-imide (11): MS (FAB) found: m/z 801.4 (100, M$^+$+1); $^1$H NMR (400 MHz, 5.0 mg/mL CDCl$_3$, δ ppm): 9.61, 9.20 and 8.50 (each s, 1H, 5-H, 10-H and 20-H); 8.18 and 7.76 (each s, 1H, 2×phenyl-H); 5.70 (m, 2H, J=9.8 Hz, N—CH$_2$); 5.36 (d, J=9.1 Hz, 1H, 17-H); 4.34 (q, J=7.1 Hz, 1H, 18-H); 3.92, 3.87, 3.83, 3.56, 3.25 and 3.19 (each s, 3H, 4×CH$_3$ and 2×CO$_2$CH$_3$); 3.77 and 3.66 (each q, J=8.4 Hz, 2H, 3- and 8-CH$_2$CH$_3$); 2.67 (m, 1H, 1×17CH$_2$CH$_2$CO$_2$CH$_3$); 2.39 (m, 2H, 1×17CH$_2$CH$_2$CO$_2$CH$_3$ and 1×17CH$_2$CH$_2$CO$_2$CH$_3$); 2.37 (s, 3H, phenyl-CH$_3$); 1.99 (m, 1H, 1×17CH$_2$CH$_2$CO$_2$CH$_3$); 1.77 (d, J=7.2 Hz, 3H, 18-CH$_3$); 1.72 and 1.68 (each t, J=8.0 Hz, 3H, 3- and 8-CH$_2$CH$_3$); 0.20 and −0.01 (each br s, 1H, 2N—H).

Per-acetylated Lactose-Chlorin conjugate joined with diene linkage (14): To a solution of 220 mg (0.36 mmol) of 3 and 330 mg (0.50 mmol) of O-allyl-sugar 13 in 10 ml of dichloromethane, 50 mg (0.06 mmol) of Grubbs's catalyst was added. The reaction mixture was stirred under argon for 48 h. After evaporating the solvent, the residue was purified by silica plate chromatography, eluting with 60% ethyl acetate in cyclohexane. The title compound was obtained in 10% yield (50 mg). WV-vis in CH$_2$Cl$_2$, $\lambda_{max}$ (nm, ε): 694 (4.5×10$^4$), 544 (2.1×10$^4$), 507 (7.6×10$^3$), 417 (1.5×10$^5$), 362 (4.5×10$^4$); $^1$H NMR (400 MHz, 5.0 mg/mL CDCl$_3$ δ ppm) showing a diastereomeric mixture: 9.58, 9.18 and 8.48 (each s, 2H, 2×5-, 10- and 20-H); 7.16–3.82 (each m, total 44H, 2×14 sugar H, 2×17-H, 2×18-H, 12H for (2'-butadiene)); 3.76 and 3.64 (each q, J=7.4 Hz, total 8H, 2×3- and 8-CH$_2$CH$_3$); 3.77–3.60 (m, total 4H, 2×4'-CH$_2$O); 3.79, 3.56, 3.24 and 3.17 (each s, 6H, 2×2-, 7- and 12-CH$_3$ and 2×CO$_2$CH$_3$); 2.65 (m, 2H, 2×17CH$_2$CH$_2$CO$_2$CH$_3$); 2.38 (m, 4H, 2×17CH$_2$CH$_2$CO$_2$CH$_3$ and 2×17CH$_2$CH$_2$CO$_2$CH$_3$); 2.18–1.99 (m, total 44H, 2×7×COCH$_3$ and 2×1× 17CH$_2$CH$_2$CO$_2$CH$_3$); 1.94 (m, 18H, 2×18-CH$_3$, 2×3-CH$_2$CH$_3$ and 8-CH$_2$CH$_3$); 0.21 (br s, total 4H, 4×N—H).

Lactose-Chlorin conjugate joined with diene linkage (15, 4a): To a solution of 45 mg (0.035 mmol) of 14 in 20 ml of dichloromethane, 300 μl of 1M NaOMe in MeOH was added, and the reaction mixture was stirred under argon for 1 h. After the standard work-up, the product so obtained was crystallized with CH$_2$Cl$_2$/hexanes to afford the title compound in 86% yield (30 mg). MS (FAB) found: m/z 1000.4 (100, M$^+$+1); $^1$H NMR (400 MHz, 5.0 mg/mL CDCl$_3$, δ ppm) showing a diastereomeric mixture in a very aggregated form: 9.57, 9.29 and 8.79 (each s, total 6H, 2×5-, 10- and 20-H); 6.72–2.64 (each m, total 56H, 28 sugar H, 2×17-H, 2×18-H, 16H for linker-H and 8H for 2×3- and 8-CH$_2$CH$_3$); 3.66, 3.38, 3.23 and 3.09 (each s, 6H, 2×2-, 7-, 12-CH$_3$ and 2×CO$_2$CH$_3$); 2.63–2.09 (m, total 8H, 2×17CH$_2$CH$_2$CO$_2$CH$_3$ and 2×17CH$_2$CH$_2$CO$_2$CH$_3$); 1.95 (m, total 2H, 2×17CH$_2$CH$_2$CO$_2$CH$_3$); 1.71 (m, 6H, 2×18-CH$_3$); 1.62 and 1.54 (each t, 6H, 2×3- and 8-CH$_2$CH$_3$); −0.11 and −0.31 (each br s, total 4H, 4×N—H).

Gal-1 Interaction: In this procedure Gal-1 was alkylated with iodo-acetamide (Allen, H. J., Sucato, D., Woynarowska, B., Gottstine, S., Sharma, A., Bernacki, R. J., Role of Galeptin in Ovarian Carcinoma Adhesion in Extracellular Matrix in vitro, J. Cell. Biochem., 43, 43–57, 1990) to eliminate the thiol requirement for retention of carbohydrate-binding activity. Coupling of alkylated galaptin to Horseradish peroxidase (HRP) was carried out by a two-step glutaraldehyde procedure as described by Engvall (Engvall E., Enzyme Immunoassay ELISA and EMIT, Methods in Enzymology, 70, 419–439, 1980). The galactin-peroxidase conjugate was prepared in 50% glycerol-1% BSA and stored at −20° C. until use. The binding of the Gal-1 to photosensitizers with and without the galactose moiety was measured by an indirect ELISA method as described by Chen et al. (Chen, Y., Jain, R. K., Chandrasekaran, E. V., Matta, K. L., Use of Sialylated or Sulfated Derivatives and Acrylamide Copolymers of Gal Beta 1,3GalNAc Alpha- and GaINAc Alpha- to Determine the Specificities of Anti-T and Anti-Tn Antibody Levels in Cancer Patients, Glycoconjugate J., 12, 55–62, 1995). The microtiter wells (Dynatech Laboratories, Chantilly, Va.) were coated with 2 μg asial fetuin (Sigma) in 100 μl of 0.1M sodium carbonate, 0.2% $NaN_3$, pH 9.6 at 37° C. for 3h. The plates were tightly covered with parafilm and stored at 4° C. for use within three weeks. The optimal dilution for Gal-1HRP conjugate was determined by checker-board titration. For studying the effect of saccharides and their conjugates, 60 μl aliquots of diluted Gal-1-HRP conjugate containing 1.4 μg of Gal-1 were mixed separately in duplicate with 60 μl dilute buffer as well as serially diluted test compounds and incubated for 1 h at 37° C. A 100 μl aliquot was transferred to the microtiter wells, which had been coated with asials Fetuin, blocked and washed. The plates were then incubated for 1 h at 37° C. followed by color development with ABTS (Kirkegaard & Perry lab. Gaithersburg, Md.) and reading at 405 nm on an ELISA reader.

Figure 15:
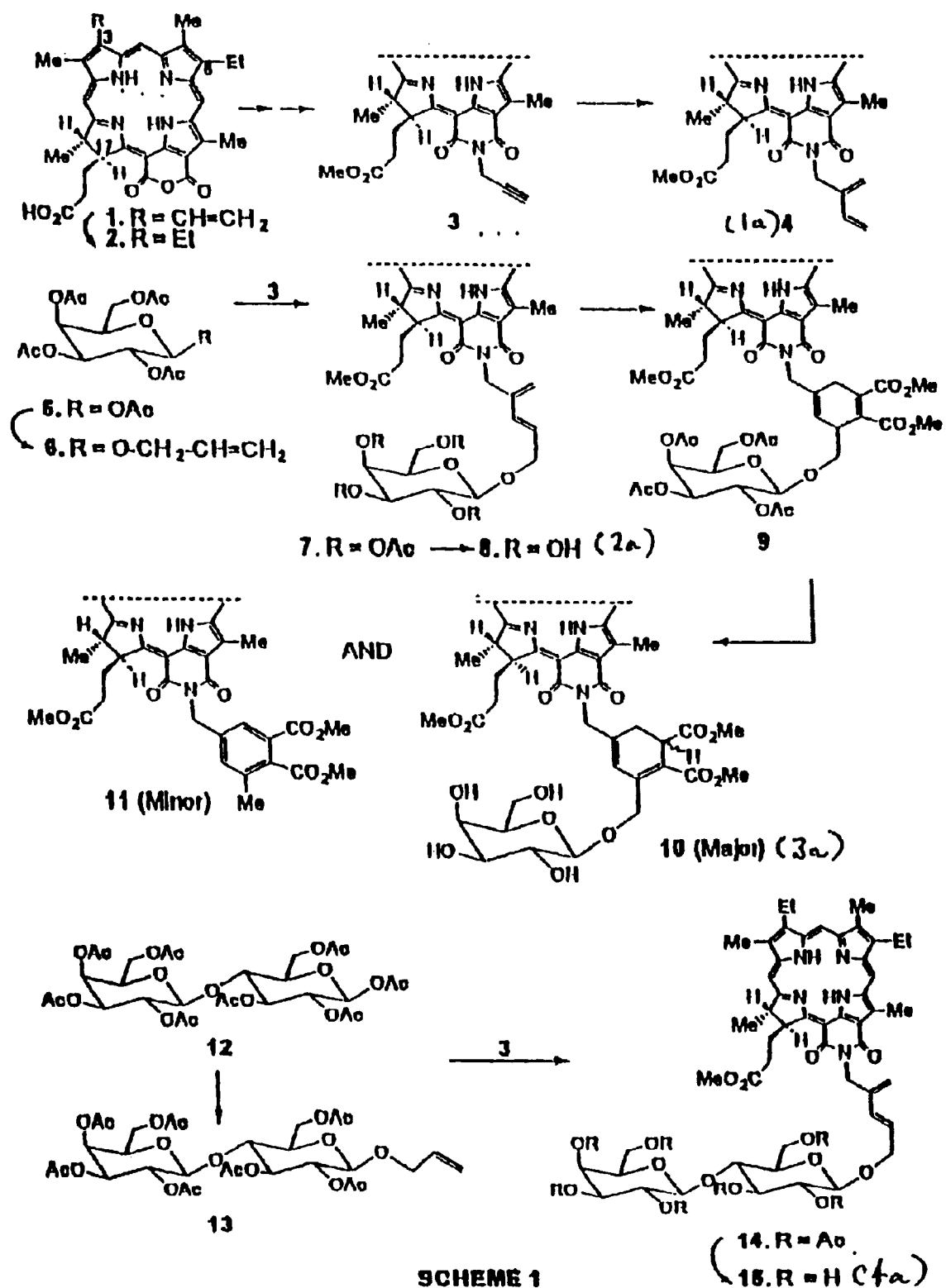
FIG. 15 shows structural equations "Scheme 1" for preparation of compounds 2–15 from starting compound 1.
Figure 16:
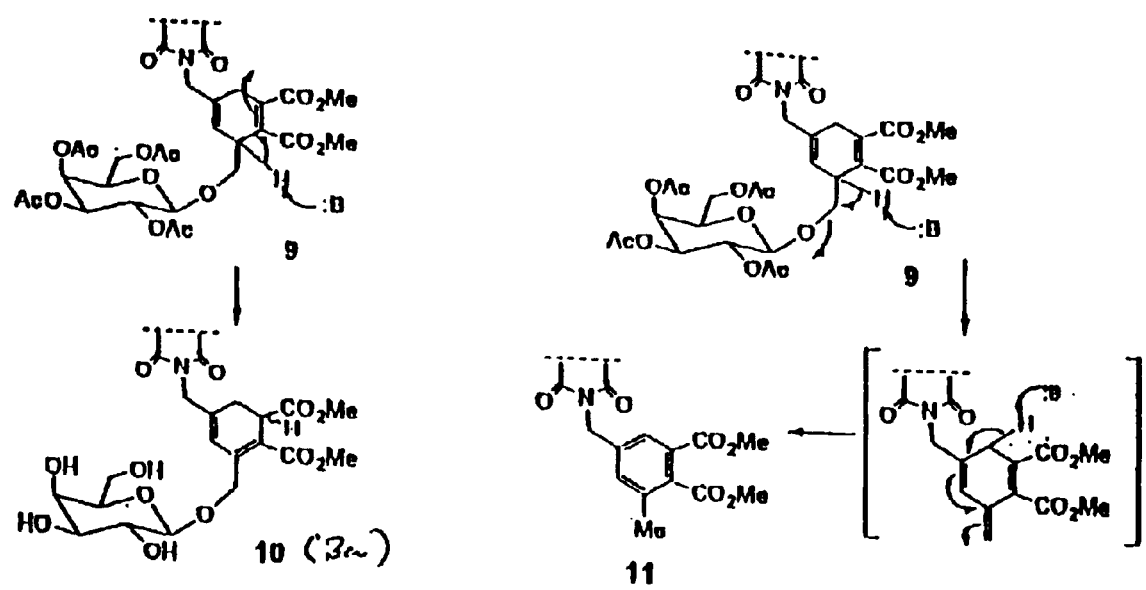
FIG. 16 shows structural equations "Scheme 2" for proposed mechanisms of preparation of compounds 10 (3a) and 11 from compound 9.
Figure 17:
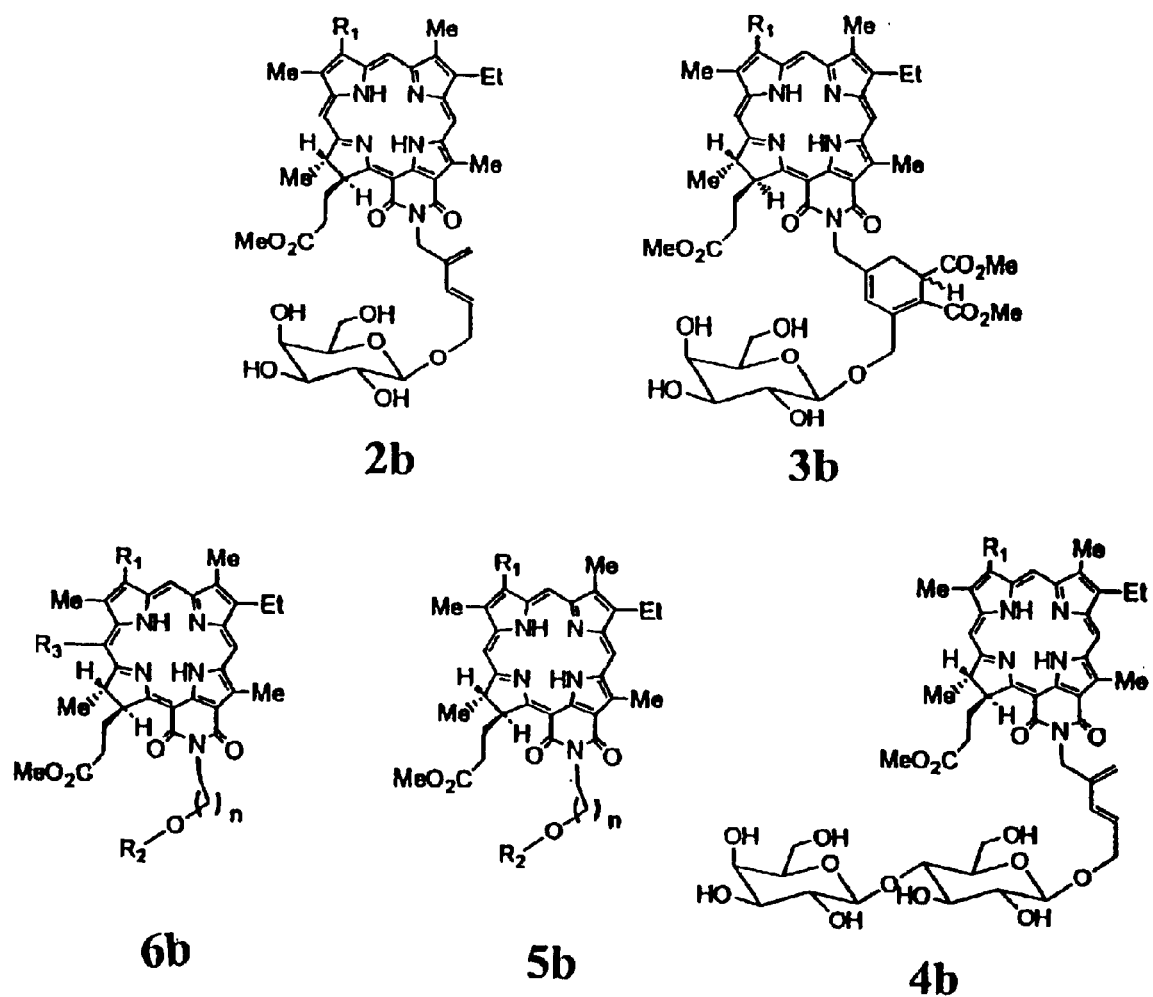
FIG. 17 shows compounds 2b–6b where 2b–4b are analogs of compounds 2a–4a having permitted variable $R_1$, $R_2$, and $R_3$ groups where: $R_1$=alkyl, aryl, alkyl ether, or various carbohydrates linked with ether or amide bonds; $R_2$=alkyl, aryl or alkyl ether or oligosaccharides where n is an integer of 1–12; and $R_3$=H or alkyl, alkyl ether or oligosaccharide.

In Vitro Studies:

In initial experiments, the in vitro photosensitizing activity of photosensitizers 1a and the corresponding carbohydrate analogs 2a, 3a and 4a (alternatively numbered 4, 8, 10 and 15 in FIGS. 15 and 16 for convenience in following preparative flow) was determined in two cell lines; Molt-4 human leukemic T-cells (Morgan, J., Potter, W. R., Oseroff, A. R., Comparison of Photodynamic Targets in a Carcinoma Cell Line and its Mitochondrial DNA-Deficient Derivatives, Photochem. Photobiol., 70, 747–757, 1999) and the radiation induced fibrosarcoma (RIF) tumor cell. Both cell lines are known to have some expression for Galectin-1 (Sacchettini, J. C., Baum, L. G. and Brewer, C. F., Multivalent Protein-carbohydrate Interactions. A New Paradiagm for Super Molecular Assembly and Signal Transduction, Biochemistry, 40:3009–3015, 2001). The Molt-4 cells were grown in RPMI 1640 5% FCS (Fetal calf serum) in 100% humidity with 5% $CO_2$. Cells were transferred to phenol red free (PRF) RPMI 1640 media with 1% FCS and plated at $2.5 \times 10^4$ cells/well. After 3 hours incubation in the dark, the cells were washed once with PBS and re-suspended in prf RPMI 1640 with 1% FCS. These cells were then illuminated with a 1000W Quartz Halogen Lamp with IR and bandpass dichroic filters to allow light between 400 nm–700 nm, at a dose rate of 16 mW/cm$^2$ at 695 nm. The RIF tumor cells were grown in alpha-DMEM with 10% fetal calf serum, penicillin and streptomycin. Cells were maintained in 5% $CO_2$, 95% air and 100% humidity. For determining the PDT efficacy, these cells were plated in 96-well plates and a density of $1 \times 10^4$ cells well in complete media. After overnight incubation to allow the cells to attach the photosensitizers 14 were individually added at variable concentrations. After a 3 hr incubation in the dark at 37° C., the cells were washed once with PBS, then irradiated with the same light source as above (Molt-4 procedure), and the optimal cell kill was obtained at a concentration of 1.0 μM. After PDT the cells were washed once and placed in complete media and incubated for 48 hrs. Then 10 μl of 4 mg/ml solution of 3-(4,5-dimethylthiazol-2-yl)-2,5-diphenyltetrazoliumbromide dissolved in PBS (Sigma, St. Louis, Mo.) was added to each well (Kessel, D., Luo, Y., Photodynamic Therapy: A Mitochondrial Inducer of Apoptosis, Cell Death Differ. 6:28–35, 1999; MacDonald, I., Morgan, J., Bellnier, D. A., Paszkiewicz, G. M., Whitaker, J. E., Litchfield, D. J. Dougherty, T. J., Subcellular Localization Patterns and their Relationship to Photodynamic Activity of Pyropheophorbide-a Derivatives, Photochem. Photobiol., 70, 789–997, 1999). After 4 hr incubation at 37° C. the MTT+media were removed and 100 μl DMSO was added to solubilize the formazin crystals. The 96-well plate was read on a microtiter plate reader (Miles Inc. Titertek Multiscan Plus MK II) at an absorbance of 560 nm. The results were plotted as percent survival of the corresponding dark (drug no light) control for each compound tested. Each data point represents the mean from 3 separate experiments, and the error bars are the standard deviation. Each experiment was done with 5 replicate wells.

For determining the galectin target-specificity of the carbohydrate conjugates the Molt-4 cells were incubated either with galactose or lactose at variable concentrations before treating with photosensitizers and light. In a typical experiment, lactose or galactose was added at various concentrations (0–100 μM) to the cells and incubated for 1 hr. The cells were then washed once with phosphate buffer saline (PBS), carbohydrate conjugates were then added, and the cells were again incubated for an additional 3 hrs. After treating with light, the cells were re-suspended in fresh media and incubated for 48 hrs. MTT was added to the cells and incubated for an additional 4 hrs. Dimethylsulfoxide (100 μl) was then added to each well to dissolve the formazin crystals. The plates were read on a 96 well plate reader at an absorbance of 560 nm. The data are in replicates of 6 wells and are normalized to control cells (light, no drug). In another set of experiments, a similar procedure was followed, except, the cells were not washed before the light treatment.

Variable Galectin Expression:

In order to test the galectin-specificity of the carbohydrate conjugates, the uptake and photosensitizing efficacy of photosensitizers 1 and 4 was investigated in two cell lines; B16-F1 and J774A.1 known for low (15–20%) and high galectin-expression (80–85%) respectively 37. The cells were grown in DMEM with 10% FCS, maintained in 5% $CO_2$, 95% air and 100% humidity. For uptake studies $1 \times 10^6$ cells were plated in 60 mm dishes. After 24 hours, photosensitizer 1 or the corresponding lactose conjugate 4 (1.0 μM each) was added and incubated for 3 and 24 hrs, cells were washed once with PBS and then harvested using of 2.0 mM K+EDTA (2 ml) and kept at 4° C. for 30 minutes. The cells were then gently removed from the dishes, 1.0 ml aliquots were transferred into 1 cm quartz cuvettes and their fluorescence was read on a PT1model ALBHA1 fluorimeter, at 701 nm using an excitation of wavelength of 414 nm. Protein determinations were done using Bio-rad protein assay, protein levels were determined from a standard curve. The data was represented as fluorescence/μg protein.

For determining photosensitizing efficacy in B16-F1 and J774A.Cell were plated at $1 \times 10^4$ and $2 \times 10^4$ cells per well respectively in 96 well plates. After overnight incubation, compounds 1 and 4 at the same concentration (0–2 μM) were added. After further 3 hr incubation, cells were washed with PBS and irradiated with white light (0–4 joules). Free lactose (100 μM) was added to test the effect of competitive inhibition of galectin binding on these cells. The cells were then incubated in complete media for 48 hrs and assayed for survival using the standard MTT assay.

Intracellular Localization:

For investigating the difference in sites of localization between the photosensitizers with and without carbohydrate moieties, the fluorescence light microscopy experiments were performed in Molt-4 and RIF tumor cell lines. In a typical experiment, cells were imaged at 100× on an inverted fluorescence microscope (Carl Zeiss Inc. Axiovert 35.W.Germany) with a charged-coupled device camera (Dage-MTI, model 104722-02). Images were captured and processed by computer using Image-1 image processing software (Universal Imaging Corp., version 4.0, WestChester, Pa.). The photosensitizer fluorescence was assessed by using 530–585 nm excitation and 615 nm long-pass filter to measure emission while 338–378 nm excitation for DPH, and a 450 nm emission filter for emission (400 nm dichroic). By following similar methodology, the localization studies were also performed in RIF tumor cells. Cells were incubated in the dark under the same conditions used for evaluating PDT efficacy. In addition, ⊞-(4-trimethylammonium)-6-phenyl-1,3,5-hexatriene (TMA-DPH), a hydrophobic fluorescent probe which interacts with living cells by instantaneous incorporation into plasma membrane and becomes fluorescent (Illinger, D., and Kuhry, J. G., The Kinetic Aspects of Intracellular Fluorescence Labeling with TMA-DPH Support the Maturation Model for Endocytosis in L929 Cells, The Journal of Cell Biology, 125:783–794, 1994), was added for the last 5 min of the incubation, cells were washed once with PBS and transferred to a microscope slide for imaging.

The Gal-1 target specificity of the galactose conjugate 3a and 4a was further confirmed by incubating the cells with galactose and lactose before treating with the photosensitizers and light. In a typical experiment lactose or galactose was added at various concentrations (0–100 $\mu$M) to the cells and incubated for 1 hr. The cells were then washed once with phosphate buffer saline (PBS), photosensitizer 3a was then added, and the cells were again incubated for an additional 3 hrs. After treating with light the cells were re-suspended in fresh media and incubated for 48 hrs. 3-(4,5-dimethylthiazol-2-yl)-2,5-diphenyltetrazoliumbromide (0.4 mg) dissolved in 10 $\mu$l of PBS (Sigma, St. Louis, Mo.) was added to the cells and incubated for an additional 4 hrs. Dimethylsulfoxide (100 $\mu$l) was then added to each well to dissolve the formazin crystals. The plates were read on a 96 well plate reader (Miles Inc. Titertek Multiscan Plus MK II) at an absorbance of 560 nm. The data are in replicates of 6 wells and are normalized to control cells (light, no drug).

In Vivo Studies:

Both conjugated and non-conjugated photosensitizers (1–4) were evaluated for their in vivo tumor response in C3H mice implanted with RIF tumors. In brief, C3H/HEJ mice were injected intradermally with $2 \times 10^5$ RIF cells in 30 $\mu$l HBSS w/o Ca$^{+2}$ and magnesium, into the flank and allowed to grow until they were 4–5 mm in diameter. The day before tumors were treatment size, the mice were injected with 0–5 $\mu$lmoles/kg of compounds 1–4. At 24 hours post-injection the mice were anesthetized with Ketamine and Xylazine, and restrained on plastic holders, treated with laser light from an argon pumped dye laser at 700 nm for a total fluence of 135 J/cm$^2$ at a fluence rate of 75 mW/cm$^2$. The mice (6 mice/group) were checked daily, the tumors were measured using two orthogonal measurements L and W (perpendicular to L) and the volumes were calculated using the formula V=LxW$^2$/2 and recorded. Mice were considered cured if there was no palpable tumor at 90 days post PDT treatment.

Lactose inhibition studies were performed by injecting compounds 1–4 at a concentration of 5.0 $\mu$moles/kg. Lactose at hundred-fold excess was administered either immediately after injecting the photosensitizers or at 1 hour prior to light treatment.

Figure 3:
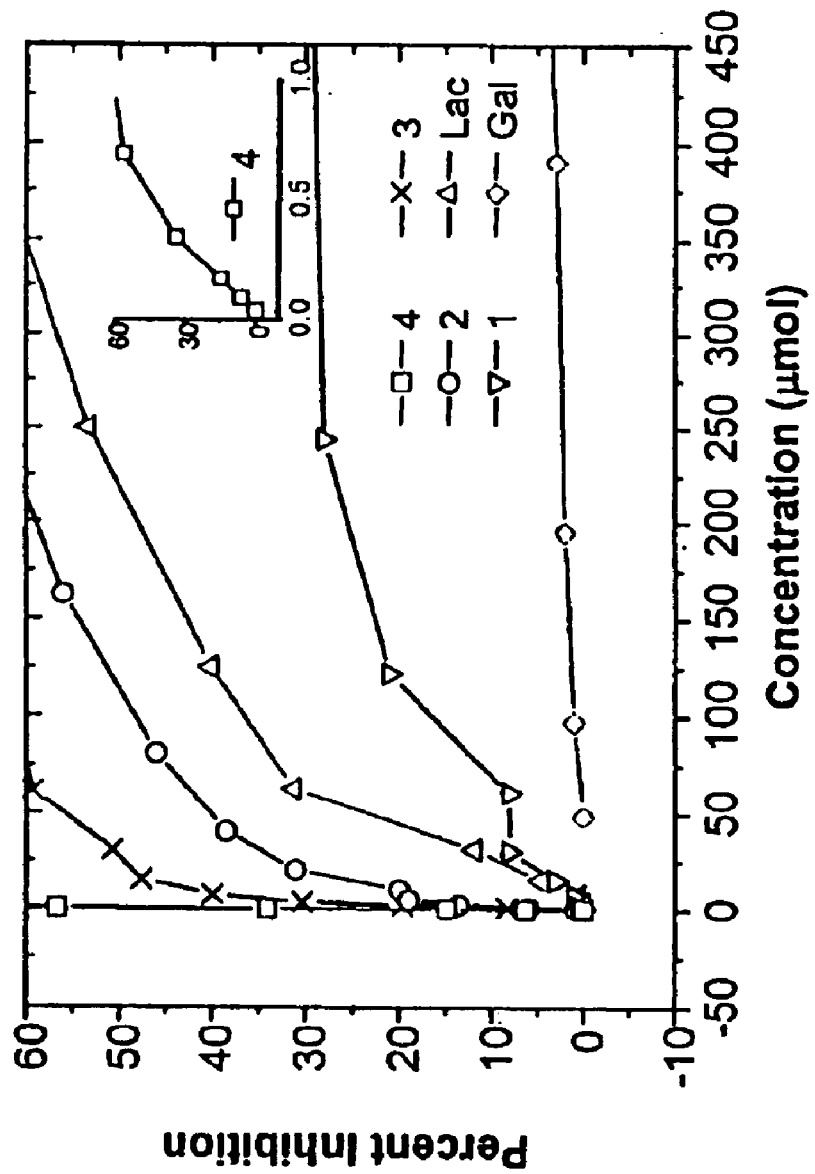
FIG. 3 is a graph showing inhibition of Gal-1 binding: galactose (only 3% inhibition at 450 $\mu$M); lactose ($I_{50}$: 257 $\mu$M); photosensitizer 1 (only 29% inhibition at 450 $\mu$M); galactose conjugate 2 ($I_{50}$: 114 $\mu$M); galactose conjugate 3 ($I_{50}$: 22 $\mu$M); lactose conjugate 4 ($I_{50}$: 0.54 $\mu$M, see inset).

Galectin Inhibition Binding Studies ($I_{50}$): In order to explore the feasibility of Gal-mediated delivery of the photosensitizers to tumor, the specificity and sensitivity of Gal-1 binding to the conjugate photosensitizers' $\beta$-galactoside subunit was investigated. FIG. 3 presents inhibition curves obtained for galactose, lactose and the photosensitizers with or without carbohydrate moieties. The Iso values for the galactose derivatives (compounds 2 and 3) were 114 and 22 $\mu$M and for lactose alone it was found to be 257 $\mu$M. The photosensitizer 4, without the galactose moiety and galactose itself were ineffective, exhibiting only 29% and 3% inhibition respectively at the concentrations up to 450 $\mu$M. To our surprise, compared to the galactose conjugate 2, photosensitizer 4 in which the galactose was replaced by a lactose moiety produced a remarkable 40 fold increase in $I_{50}$ inhibition (0.5 $\mu$M) binding affinity. These results prompted us to evaluate these compounds for in vitro photosensitizing efficacy and to determine a possible correlation with their Gal-1 inhibition binding abilities.

Figure 4:
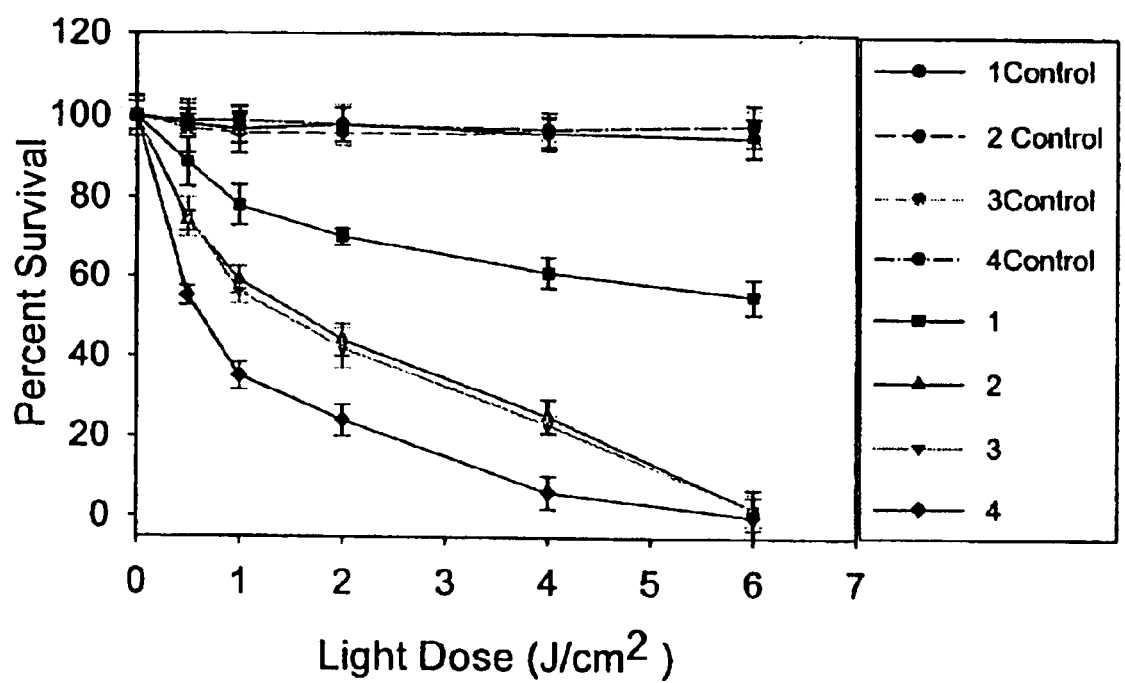
FIG. 4 is a graph showing in vitro photosensitizing efficacy of purpurinimide 1a and the related carbohydrate conjugates 2a, 3a, and 4a in Molt-4 cells at a concentration of 2.0 $\mu$M. Control: Photosensitizer alone, no light treatment.

In Vitro Photosensitizing Efficacy: In order to select the optimal drug concentration for in vitro studies, the photocytotoxicity of one of the carbohydrate conjugates 3a was determined in Molt-4 cells at variable concentrations (FIG. 4). A concentration of 2.0 $\mu$M was chosen as optimum. Viability was measured by the MTT assay. The other photosensitizers (with and without carbohydrate conjugates) were then evaluated at the same concentration. Compared to the non-galactose analog 1a, both chlorin-galactose conjugates 2a and 3a showed significant increases in photosensitizing efficacy (FIG. 3). It was interesting to observe that decreasing the flexibility of the diene system (compound 2a) by converting it into the corresponding DMAD analog 3a while producing a significant increase in Gal-1 inhibition activity, exhibited similar PDT efficacy (FIG. 2). However, compared to photosensitizers 2a and 3a the corresponding lactose conjugate 4a that showed a significant increase in Gal-1 inhibition affinity was also found to be a better pbotosensitizer (FIG. 4).

Figure 5:
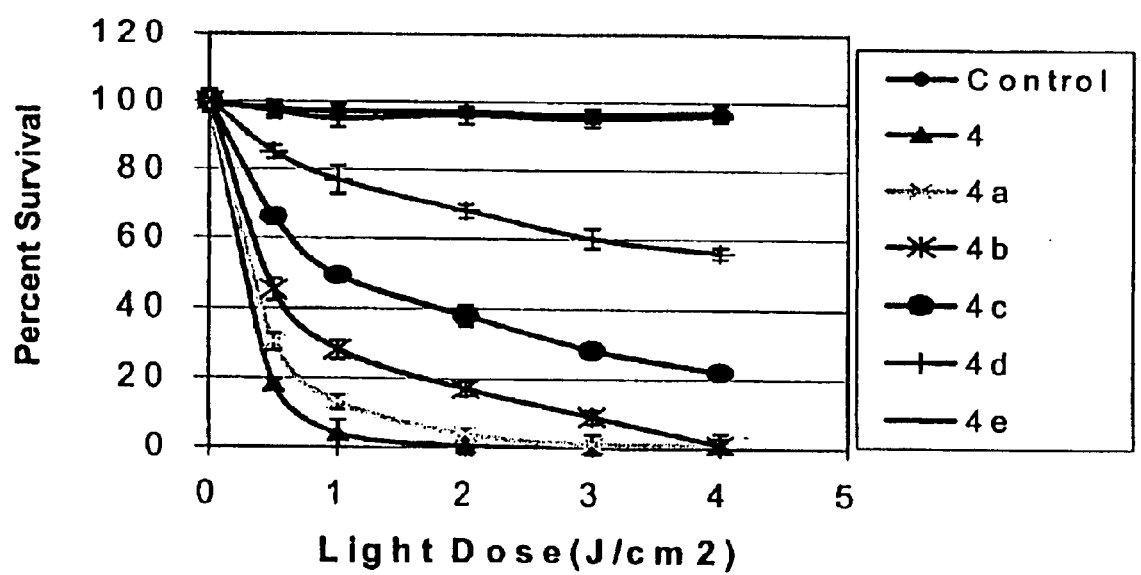
FIG. 5 is a graph showing comparative in vitro photosensitizing efficacy of the lactose conjugate 4 in Molt-4 cells with and without incubating with free lactose at variable concentrations (4: photosensitizer 4 alone; 4a: 4 and lactose ratio 1 to 0.5, 4b: 4 and lactose ratio 1 to 1, 4c: 4 and lactose ratio 1 to 5; 4d: 4 and lactose ratio 1 to 10; 4e: 4 and lactose ratio 1 to 100). Control: Photosensitizer alone, no light treatment.
Figure 6:
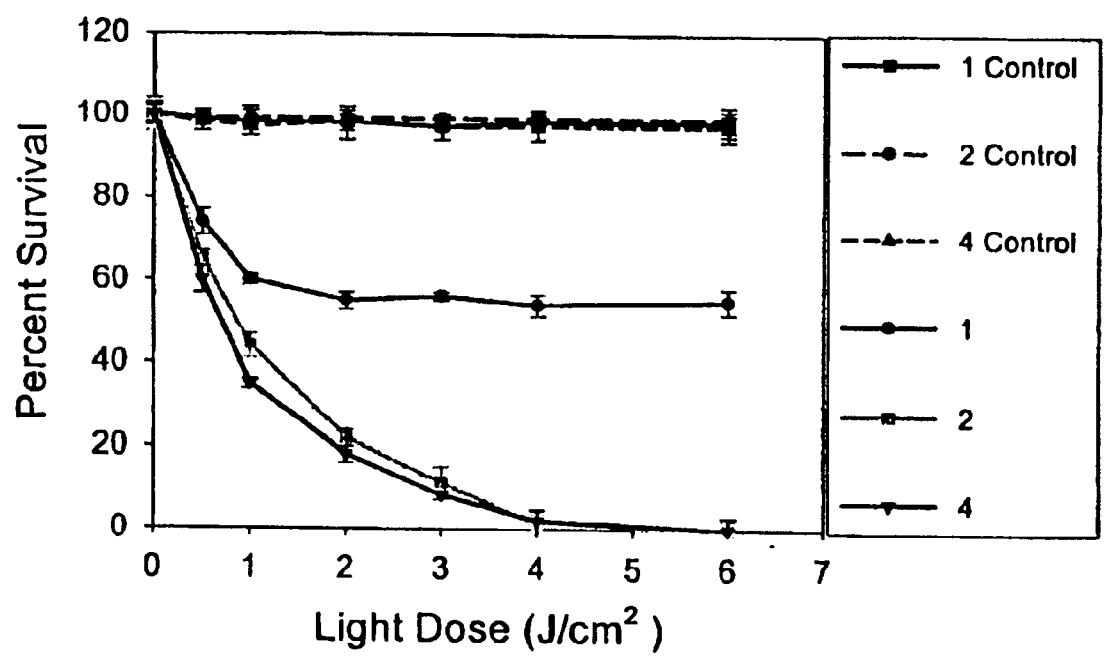
FIG. 6 shows in vitro photosensitizing activity of purpurinimide 1 and the corresponding carbohydrate conjugates 2 and 4 in RIF tumor cells at a concentration of 2.0 $\mu$M. Control: Photosensitizer alone, no light treatment.
Figure 7:
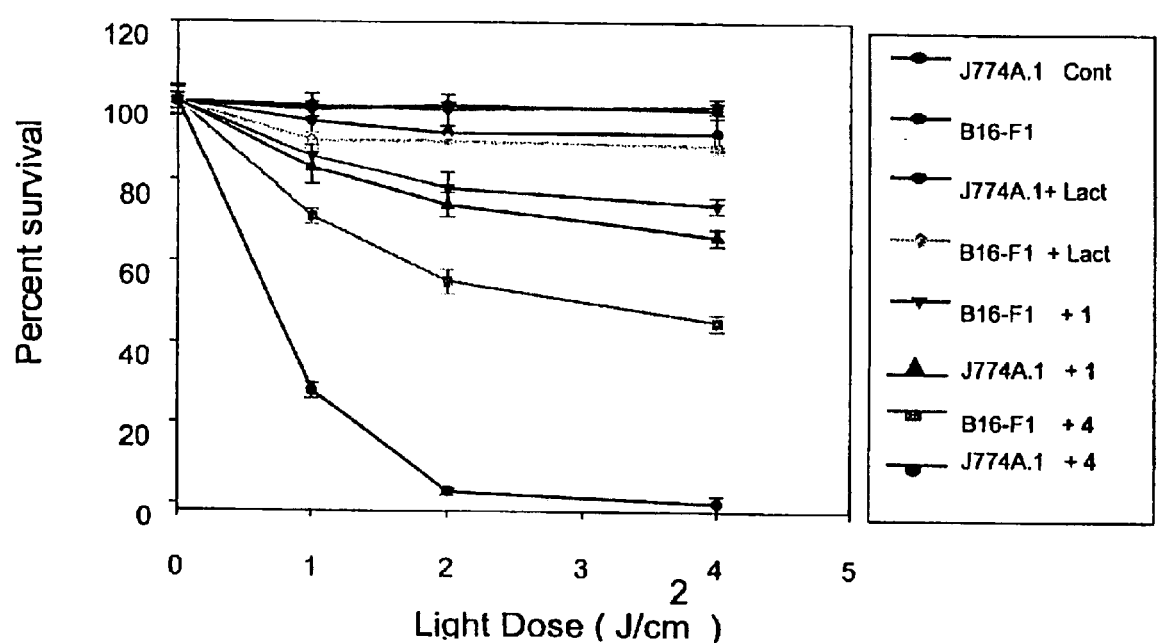
FIG. 7 is a graph showing comparative in vitro photosensitizing efficacy of non-conjugated purpurinimide 1 (1.0 $\mu$M) and the lactose conjugate 4 (1.0 $\mu$M) in B16-F1 and J774A.1 cells with a low (15–20%) and high (80–85%) Gal-1 expression respectively. Control: Photosensitizer 4 alone, no light treatment.
Figure 8A:
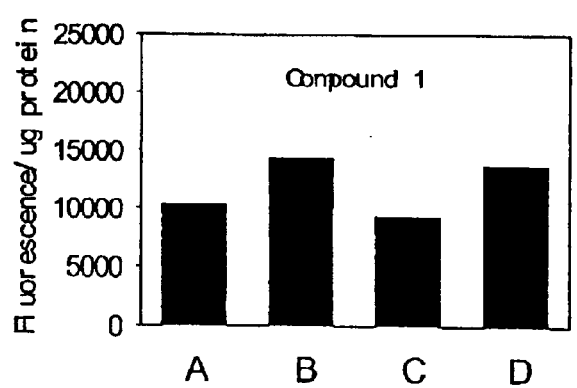
FIG. 8a shows comparative uptake of purpurinimide 1 in B16-F1 and J774A.1 cells with low (15–20%) and high (80–85%) Gal-1 expression respectively. A: B16-F1(3h); B: B16-F1(24h); C: J774A.1(3h); and D: J774A.1(24h).
Figure 8B:
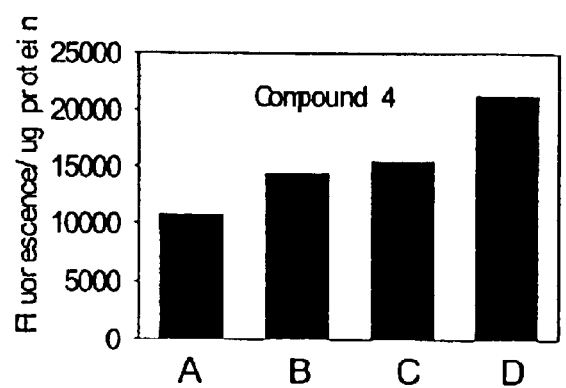
FIG. 8b shows comparative uptake of purpurinimide 1 lactose conjugate 4a in B16-F1 and J774A.1 cells with low (15–20%) and high (80–85%) Gal-1 expression respectively. A: B16-F1(3h); B: B16-F1(24h); C: J774A.1(3h); and D: J774A.1(24h).

The inhibition of in vitro photosensitizing efficacy of photosensitizer 1a and the related carbohydrate analogs 2a, 3a and 4a was investigated in Molt-4 cells incubated with galactose and lactose at various concentrations (without washing). As expected, galactose alone, due to its limited galectin-1 inhibition binding efficacy (3.29% at 450 $\mu$M), did not result in any inhibition in PDT activity, whereas lactose at increasing concentrations produced a significant decrease in photosensitizing efficacy. Replacing photosensitizer 3a with lactose conjugate 4a gave similar results (FIG. 5). Carbohydrate conjugated photosensitizers 2a, 3a and 4a with lactose in a ratio of 1:100, produced a complete inhibition in PDT efficacy. These data further indicate a possibility that galactose and lactose conjugates bind to the $\beta$-galactose binding site of the galectin. Under similar experimental conditions, addition of free lactose did not produce any change in photocytotoxic ability of non-conjugated analog 1a and the results obtained from both the experiments were overlapping. A decreased phototoxicity by carbohydrate conjugate was also observed on incubating the cells for three hours before light exposure after PBS washing. Phototoxicity studies were also performed in RIF tumor cells. As can be seen in FIG. 6, the unconjugated compound 1 killed approximately 40% of the cells, whereas conjugated analogs 2a and 4a both produced 100% cell kill at a light dose of 4 J/cm.$^2$ Our next step was to evaluate the specificity of these carbohydrate conjugates in cell lines known for variable galectin expression. For this study two cell lines B16-F1 and J774A.1 with low and high galectin-1 expression respectively were treated with non-conjugated photosensitizer 1a and the corresponding lactose conjugate 4a, and the results are summarized in FIG. 7. As can be seen, compared to photosensitizer 1a lactose conjugate 4a produced enhanced phototoxicity in high galectin-1 expressing J774A.1 cells. Addition of free lactose almost completely inhibited the PDT efficacy of compound 4a in both cell lines, presumably by blocking conjugate 4a galectin binding-site. The drug uptake of compound 1a and the related lactose conjugate 4a was also investigated in these two cell lines. The unconjugated photosensitizer 1a showed similar uptake in both cell lines with increased level of uptake at 24 hr in both cells. In contrast to 1a, compound 4a showed increased uptake in J774 A.1 cells at both timepoints, suggesting that higher galectin expression on these cells facilitated increased uptake of the lactose conjugate.

Figure 9A:
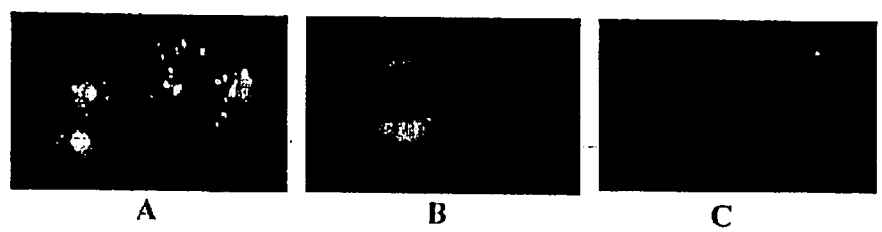
FIG. 9a is a series of photomicrographs showing comparative cellular localization of photosensitizers with and without lactose in Molt-4 cells (A: non-carbohydrate conjugate photosensitizer 1; B: lactose conjugate 4; C: 4 with free lactose (100 $\mu$M)).
Figure 9B:
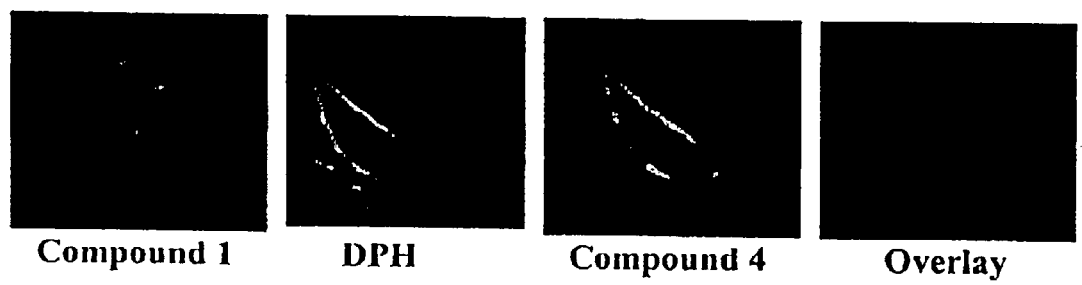
FIG. 9b is a series of photomicrographs showing comparative cellular localization of lactose conjugates 1 and 4 in RIF tumor cells with DPH.

Cellular and Intracellular Localization Studies:

In a separate experiment, Molt-4 cells, incubated for 3 hrs with photosensitizers 1a, 2a, 3a and 4a and were washed once with PBS and transferred individually to a microscope slide for imaging. The localization studies (Pendergast, R. G., Haughland, R. P., Callahan, P. J., 1-(4-(trimethylamino)-phenyl)-6-phenylhexa-1, 3, 5-triene: Synthesis, Fluorescence Properties and use as a Fluorescence Probe of Lipid Bilayers, Biochemistry, 20, 7333–7338, 1981; Kessel, D., Woodburn, K., Henderson, B., Chang, C. K., Sites of Photodamage in vivo and in vitro by a Cationic Porphyrin, Photochem. Photobiol., 62, 875–881, 1995) with conjugates produced clear evidence of their binding to the cell surface. On the other hand, the non-galactose analog 1a exhibited intracellular localization. The β-galactose conjugates (e.g., 4a) in presence of lactose at variable concentrations produced a remarkable inhibition in fluorescence intensity. No fluorescence was observed if the lactose concentration was increased to 100 μM. In preliminary in vivo screening, the photosensitizing efficacy of the carbohydrate-conjugated and non-conjugated analogs were investigated in mice bearing RIF tumors (FIG. 9B), we thought it worthwhile to determine the cellular localization characteristics of these analogs RIF cells. In order confirm the cell surface localization, comparative localization studies with DPH as a counterstain (known to bind to cell-surface) was performed. The images shown in FIGS. 9a and 9b clearly indicate intense plasma membrane fluorescence by conjugate 4a confirming its membrane binding specificity. Under similar experimental conditions, non-carbohydrate conjugate 1a did not produce such specificity and exhibited diffuse intracellular localization.

Figure 10:
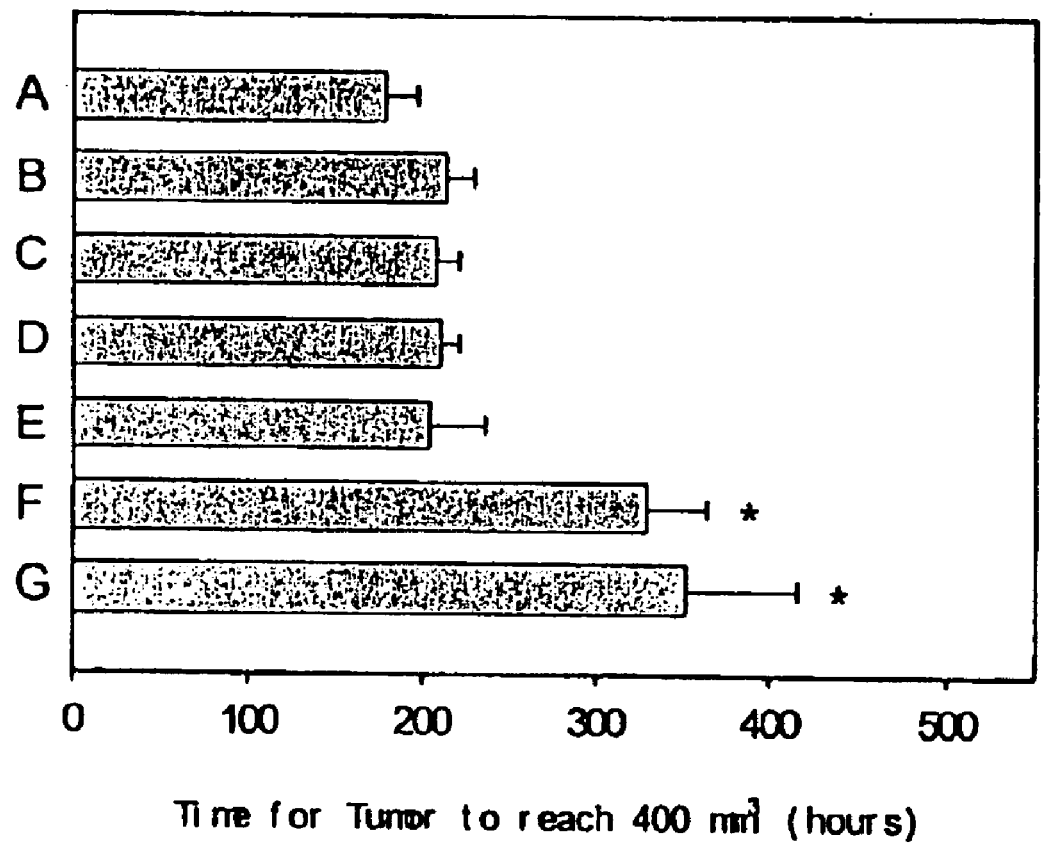
FIG. 10 is a bar graph showing in vivo photosensitizing efficacy of lactose conjugate 4 (5.0 $\mu$M/kg) with and without injecting free lactose (100-fold excess) in mice (6/group) bearing RIF tumors. A: Control (without photosensitizer and lactose); B: Compound 1+free lactose immediately post injection; C: Compound 1+free lactose 1 hr pre-PDT (i.e., 23 h post injection of the drug); D: Compound 1 (no free lactose); E: Compound 4+free lactose immediately post injection; F: Compound 4+free lactose 1 hr pre-PDT (i.e., 23 hr post injection of the drug); G: Compound 4 (no free lactose). Three out of six mice were tumor free at day 90.
Figure 11:
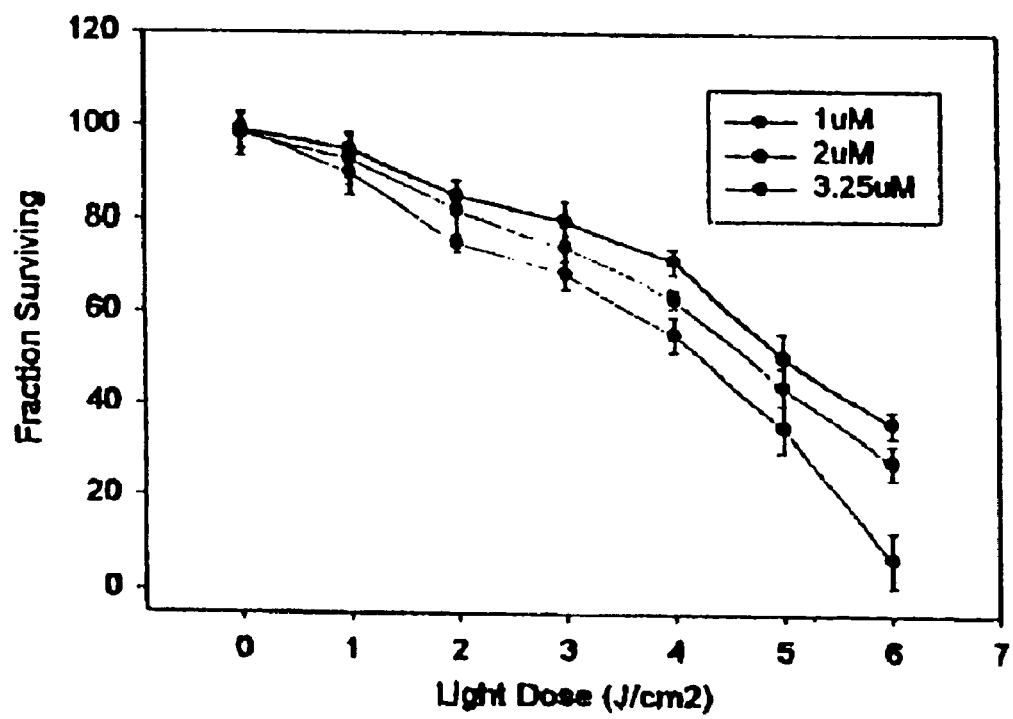
FIG. 11 shows in vitro photosensitizing efficacy of purpurinimide-galactose conjugate 3a at various concentrations.

In Vivo Photosensitizing Efficacy:

The tumor response (tumor re-growth assay) of purpurinimide 1a and the corresponding lactose analogs 4a was performed in mice bearing RIF tumors at a dose of 5.0 μM/kg (FIG. 10). Compared to the non-conjugate analog 1a which was inactive in vivo, the lactose conjugate 4a under similar treatment conditions was found to be quite effective (3/6 mice were tumor free on day 90). The additional injection of exogenous lactose at different time intervals had a significant effect on the efficacy of 4a. For example, on injecting lactose immediately following the drug administration produced a significant decrease in PDT efficacy. However, when the lactose was injected 1 hour prior to light treatment (i.e. 23 hr post-injection of the conjugate), the drug as found to be quite effective indicating that the lactose administration did not have any effective in PDT response. In a similar experiment, the non-carbohydrate conjugate 1a (with and without lactose administration) did not produce any difference on PDT efficacy and was found to be ineffective. These results suggest that when a large excess (5 fold) of lactose is injected immediately following the lactose-chlorin conjugate 4a, it had a much higher probability to bind to the target site than the conjugate and that possibly caused a remarkable decrease in PDT efficacy. However, when the lactose was injected 1 hour before the light treatment (i.e. 23h post-injection of the photosensitizer 4a), there should be a lower possibility for lactose to replace the drug which has already been bound to the specific target-site and therefore, no significant inhibition in photosensitizing efficacy was observed.

This invention includes the synthesis and the medicinal applications of the compounds illustrated in FIGS. 1, 15, 16 and 17.

What is claimed is:

1. A compound of the formula:

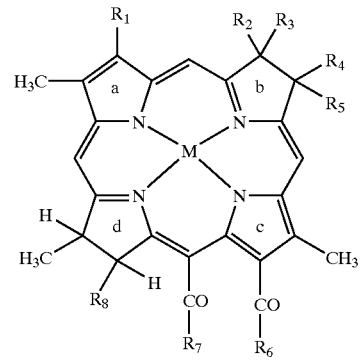

where $R_1$ is lower alkyl, vinyl, alkyl ether, aryl, lower carboxy, or —CH(OR$_9$)CH$_3$ where $R_9$ is alkyl of 1 to about 20 carbon atoms, a cyclic containing substituent containing 1 to about 20 carbon atoms connected to the a ring through a carbon-carbon or —O— bond; $R_2$ and $R_5$ are independently hydrogen or lower alkyl, $R_3$ and $R_4$ are independently —H, lower alkyl, or —OR$_{10}$, where $R_{10}$ is H or lower alkyl, or $R_3$ and $R_4$, together form a covalent bond; $R_6$ and $R_7$ taken together are =NR$_{11}$ or are independently —OR$_{11}$ where $R_{11}$ is independently —H, alkyl of 1 to about 20 carbon atoms, a cyclic containing substituent containing 1 to about 20 carbon atoms, an amide group or a mono or polysaccharide connected to =N— or —O— through at least one of a saturated or unsaturated lower alkylene group, a saturated or unsaturated heterocylic or hydrocarbon five or six membered ring, an ether linkage, an amide linkage or an ester group; $R_8$ is —CH$_2$CH$_2$COR$_{12}$ where $R_{12}$ is an amino acid residue, —NHR$_{13}$ or —OR$_{14}$ where $R_{13}$ is hydrogen, alkyl of 1 to about 20 carbon atoms, or a mono or polysaccharide connected to —NH— through at least one of a saturated or unsaturated lower alkylene group, a saturated or, unsaturated heterocylic or hydrocarbon five or six membered ring, an ether linkage, an amide linkage or an ester group and $R_{14}$ is hydrogen, or alkyl of 1 to about 20 carbon atoms, where lower alkyl includes alkyl and alkylene groups of 1 to 5 carbon atoms and alkyl includes linear, branched and cyclic unsubstituted alkyl and linear, branched and cyclic alkyl and alkylene groups substituted with hydroxy, carboxy, alkyl, vinyl, amino, amido, keto, heterocyclic, mono and polysaccharide and amino acid groups; provided that the compound contains at least one mono or polysaccharide group that will combine with galectin-1 and M is a chelated metal or is two hydrogens bound to the unsaturated nitrogens in the a and c rings.

2. The compound of claim 1 wherein $R_6$ and $R_7$ are $=NR_{11}$, where $R_{11}$ is a mono or polysaccharide connected to $=N-$ through at least one of a saturated or unsaturated lower alkylene group, a saturated or unsaturated heterocylic or hydrocarbon five or six membered ring, an ether linkage, an amide linkage or an ester group.

3. The compound of claim 2 where the saccharide is selected from the group consisting of lactose and galactose.

4. The compound of claim 2 where $R_{11}$ is:

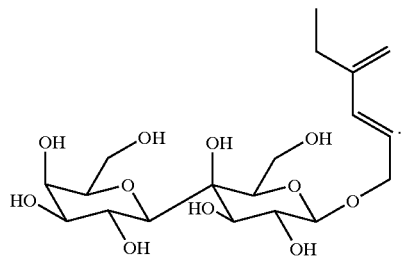

5. The compound of claim 2 wherein $R_{11}$ is:

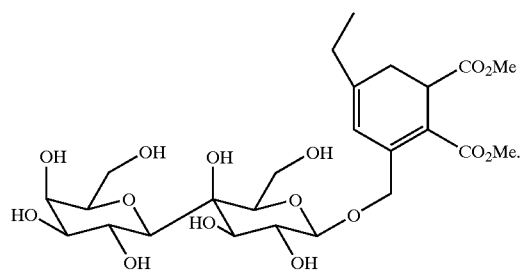

6. The compound of claim 2 wherein $R_{11}$ is:

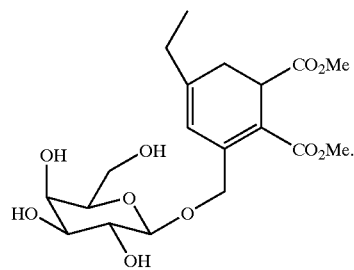

7. The compound of claim 2 wherein $R_{11}$ is:

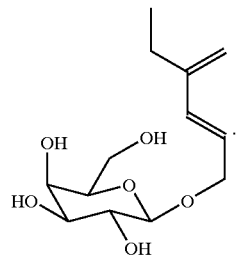

8. The compound of claim 2 where $R_{11}$ is $-CH_2-R_{15}-O-R_{16}$ where $R_{15}$ is a lower alkylene group and $R_{16}$ is lower alkyl, alkylether, or a saccharide.

9. The compound of claim 1 where $R_3$ and $R_4$ taken together form a covalent bond.

10. The compound of claim 2 where $R_3$ and $R_4$ taken together for a covalent bond.

11. The compound of claim 1 where $R_1$ and $R_5$ are ethyl.

12. The compound of claim 2 where $R_1$ and $R_5$ are ethyl.

13. The compound of claim 10 where $R_1$ and $R_5$ are ethyl.

14. The compound of claim 1 where $R_2$ is methyl.

15. The compound of claim 2 where $R_2$ is methyl.

16. The compound of claim 10 where $R_2$ is methyl.

17. The compound of claim 1 where R is $-CH_2CH_2COR_{12}$.

18. The compound of claim 17 where $R_{12}$ is $-OR_{14}$ where $R_{14}$ is lower alkyl.

19. A method for inhibiting cancer cell growth which includes the steps of contacting the cells with a compound of claim 1 and exposing the cells to light at a dose rate of from about 5 to about 50 mW/cm$^2$ at a wave length of from about 400 to about 800 nm, the cells being contacted with sufficient compound to inhibit their growth after said exposure.

20. A method for inhibiting cancer cell growth which includes the steps of contacting the cells with a compound of claim 2 and exposing the cells to light at a dose rate of from about 5 to about 50 mW/cm$^2$ at a wave length of from about 400 to about 800 nm, the cells being contacted with sufficient compound to inhibit their growth after said exposure.

21. A method for inhibiting cancer cell growth which includes the steps of contacting the cells with a compound of claim 4 and exposing the cells to light at a dose rate of from about 5 to about 50 mW/cm$^2$ at a wave length of from about 400 to about 800 nm, the cells being contacted with sufficient compound to inhibit their growth after said exposure.

22. A method for inhibiting cancer cell growth which includes the steps of contacting the cells with a compound of claim 10 and exposing the cells to light at a dose rate of from about 5 to about 50 mW/cm$^2$ at a wave length of from about 400 to about 800 nm, the cells being contacted with sufficient compound to inhibit their growth after said exposure.

23. The method for inhibiting cancer cell growth which includes the steps of contacting the cells with a compound of claim 16 and exposing the cells to light at a dose rate of from about 5 to about 50 mW/cm$^2$ at a wave length of from about 400 to about 800 nm, the cells being contacted with sufficient compound to inhibit their growth after said exposure.

24. The method of claim 19 where the cells are exposed to the compound at a solution concentration of from about 1 to about 20 $\mu$M.

25. The method of claim 20 where the cells are exposed to the compound at a solution concentration of from about 1 to about 20 $\mu$M.

* * * * *

UNITED STATES PATENT AND TRADEMARK OFFICE
CERTIFICATE OF CORRECTION

PATENT NO.        : 6,849,607 B2
APPLICATION NO.   : 10/141241
DATED             : February 1, 2005
INVENTOR(S)       : Pandey et al.

Page 1 of 1

It is certified that error appears in the above-identified patent and that said Letters Patent is hereby corrected as shown below:

Title Page, Item (75) Inventor is corrected to read:
-- Ravindra K. Pandey, Williamsville (NY);
Thomas J. Dougherty, Grand Island (NY);
Khushi L. Matta, Williamsville (NY) --.

Signed and Sealed this
Fourteenth Day of June, 2016

Michelle K. Lee
*Director of the United States Patent and Trademark Office*